(12) United States Patent  
Yerkes et al.

(10) Patent No.: US 9,237,747 B2  
(45) Date of Patent: Jan. 19, 2016

(54) HERBICIDAL COMPOSITIONS COMPRISING 4-AMINO-3-CHLORO-5-FLUORO-6-(4-CHLORO-2-FLUORO-3-METHOXYPHENYL) PYRIDINE-2-CARBOXYLIC ACID OR A DERIVATIVE THEREOF AND INSECTICIDES

(71) Applicant: Dow AgroSciences LLC, Indianapolis, IN (US)

(72) Inventors: Carla N. Yerkes, Crawfordsville, IN (US); Richard K. Mann, Franklin, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 14/205,052

(22) Filed: Mar. 11, 2014

(65) Prior Publication Data

US 2014/0274698 A1    Sep. 18, 2014

Related U.S. Application Data

(60) Provisional application No. 61/777,598, filed on Mar. 12, 2013.

(51) Int. Cl.
    *A01N 63/00*     (2006.01)
    *A01N 43/00*     (2006.01)
    *A01N 43/40*     (2006.01)
    *A01N 43/36*     (2006.01)
    *A01N 43/02*     (2006.01)
    *A01N 43/30*     (2006.01)

(52) U.S. Cl.
    CPC ...................................... *A01N 43/30* (2013.01)

(58) Field of Classification Search
    None
    See application file for complete search history.

(56) References Cited

U.S. PATENT DOCUMENTS 7,314,849 B2 *   1/2008  Balko et al. .................. 504/244
2007/0179060 A1   8/2007  Balko et al.
2010/0222221 A1   9/2010  Eckelbarger et al.
2012/0015811 A1   1/2012  Dave et al.
2012/0190551 A1   7/2012  Yerkes et al.

FOREIGN PATENT DOCUMENTS

CN         101524080     *  9/2009
JP          2011252025     *  12/2011

* cited by examiner

*Primary Examiner* — Alton Pryor

(74) *Attorney, Agent, or Firm* — Michael R. Asam; Meunier Carlin & Curfman, LLC

(57) ABSTRACT

Provided herein are synergistic herbicidal compositions containing (a) a compound of formula (I):

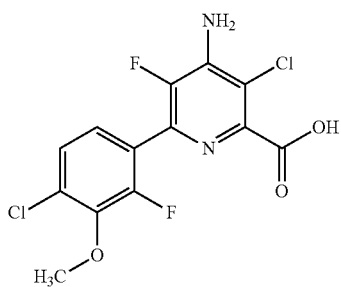

or an agriculturally acceptable salt or ester thereof and (b) insecticides, including but not limited to, acephate, carbaryl, carbofuran, cartap, chlorpyrifos, cypermethrin, dimethoate, dinotefuran, etofenprox, fenitrothion, fipronil, imidacloprid, lambda-cyhalothrin, malathion, methamidophos, piperonyl butoxide, pymetrozine, spinetoram, spinosad, sulfoxaflor and triazophos. The compositions and methods provided herein control undesirable vegetation, e.g., in direct-seeded, water-seeded and transplanted rice, cereals, wheat, barley, oats, rye, *sorghum*, corn/maize, sugarcane, sunflower, oilseed rape, canola, sugar beet, soybean, cotton, pineapple, pastures, grasslands, rangelands, fallowland, turf, tree and vine orchards, plantation crops, vegetables, industrial vegetation management (IVM) and rights-of-way (ROW).

21 Claims, No Drawings

HERBICIDAL COMPOSITIONS COMPRISING 4-AMINO-3-CHLORO-5-FLUORO-6-(4-CHLORO-2-FLUORO-3-METHOXYPHENYL) PYRIDINE-2-CARBOXYLIC ACID OR A DERIVATIVE THEREOF AND INSECTICIDES

CROSS REFERENCE TO RELATED APPLICATIONS

This application claims the benefit of U.S. Provisional Patent Application Ser. No. 61/777,598 filed Mar. 12, 2013, the disclosure of which is expressly incorporated herein by reference.

BACKGROUND

The protection of crops from weeds and other vegetation which inhibit crop growth is a constantly recurring problem in agriculture. To help combat this problem, researchers in the field of synthetic chemistry have produced an extensive variety of chemicals and chemical formulations effective in the control of such unwanted growth. Chemical herbicides of many types have been disclosed in the literature and a large number are in commercial use. However, there remains a need for compositions and methods that are effective in controlling undesirable vegetation.

SUMMARY

Provided herein are herbicidal compositions comprising a herbicidally effective amount of (a) a compound of the formula (I)

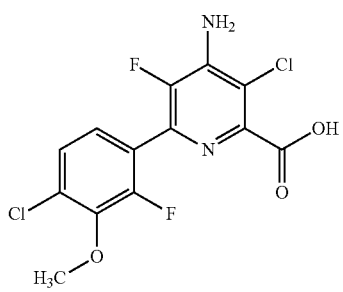

or an agriculturally acceptable salt or ester of thereof and (b) insecticides. The compositions may also contain an agriculturally acceptable adjuvant or carrier. Provided herein are also methods of controlling undesirable vegetation comprising applying (a) a compound of formula (I) or an agriculturally acceptable ester or salt thereof and (b) insecticides.

DETAILED DESCRIPTION

Definitions

As used herein, the compound of formula (I) has the following structure:

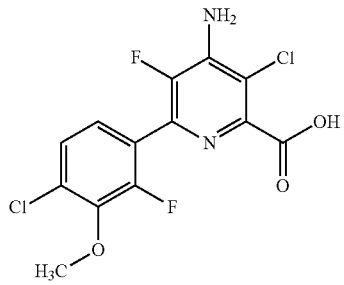

The compound of formula (I) can be identified by the name 4-amino-3-chloro-6-(4-chloro-2-fluoro-3-methoxyphenyl)-5-fluoropyridine-2-carboxylic acid and has been described in U.S. Pat. No. 7,314,849 (B2), which is incorporated herein by reference in its entirety. Exemplary uses of the compound of the formula (I) include controlling undesirable vegetation, including grass, broadleaf and sedge weeds, in multiple non-crop and cropping situations.

Insecticides are a class of pesticides used to control insects in crop and non-crop settings. Without being limited to any theory, these pesticides kill insects via multiple, different modes-of-action. Exemplary uses of insecticides include their use to control insects in cereal, legume, vegetable, fruit, row and perennial crops.

Exemplary insecticides include, but are not limited to, acephate, carbaryl, carbofuran, cartap, chlorpyrifos, cypermethrin, dimethoate, dinotefuran, etofenprox, fenitrothion, fipronil, imidacloprid, lambda-cyhalothrin, malathion, methamidophos, piperonyl butoxide, pymetrozine, spinetoram, spinosad, sulfoxaflor and triazophos.

As used herein, acephate is O,S-dimethyl acetylphosphoramidothioate and possesses the following structure:

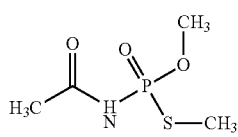

Its insecticidal activity is exemplified in Tomlin, C. D. S., Ed. *The Pesticide Manual: A World Compendium*, 15th ed.; BCPC: Alton, 2009 (hereafter "*The Pesticide Manual*, Fifteenth Edition, 2009"). Exemplary uses of acephate include its use for the control of a wide range of chewing and sucking insects in a wide variety of crops including rice. Acephate is a systemic insecticide applied at rates of about 500 to about 1,000 grams per hectare (g/ha) to control undesirable insects.

As used herein, carbaryl is 1-naphthalenyl N-methylcarbamate and possesses the following structure:

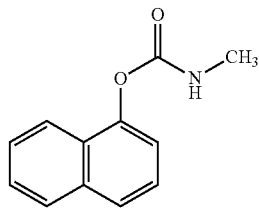

Its insecticidal activity is exemplified in *The Pesticide Manual*, Fifteenth Edition, 2009. Exemplary uses of carbaryl include its use for the control of Lepidoptera, Coleoptera and other chewing and sucking insects in over 120 different crops including rice. Carbaryl is a contact insecticide applied at rates of about 250 to about 2,000 g/ha to control undesirable insects.

As used herein, carbofuran is 2,3-dihydro-2,2-dimethylbenzofuran-7-yl methylcarbamate and possesses the following structure:

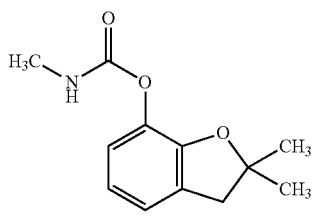

Its insecticidal activity is exemplified in *The Pesticide Manual*, Fifteenth Edition, 2009. Exemplary uses of carbofuran include its use for the control of soil-dwelling and foliar-feeding insects in a wide variety of crops including rice. Carbofuran is a systemic insecticide with contact and stomach action which is applied at rates of about 560 to about 11,200 g/ha to control undesirable insects.

As used herein, cartap is S,S'-(2-dimethylaminotrimethylene)bis(thiocarbamate) and possesses the following structure:

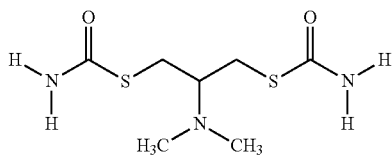

Its insecticidal activity is exemplified in *The Pesticide Manual*, Fifteenth Edition, 2009. Exemplary uses of cartap include its use for the control of chewing and sucking insects of almost all stages of development in many crops including rice. Cartap is a systemic insecticide with contact and stomach action which is applied at rates of about 400 to about 1,000 g/ha to control undesirable insects.

As used herein, chlorpyrifos is O,O-diethyl O-3,5,6-trichloro-2-pyridyl phosphorothioate and possesses the following structure:

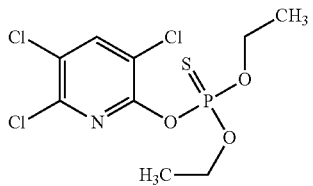 [SMILES: CCOP(=S)(OCC)Oc1nc(Cl)c(Cl)cc1Cl]

Its insecticidal activity is exemplified in *The Pesticide Manual*, Fifteenth Edition, 2009. Exemplary uses of chlorpyrifos include its use for the control of Lepidoptera, Coleoptera, Diptera and Homoptera in soil or on foliage in over 100 crops including rice. Chlorpyrifos is a non-systemic insecticide with contact, stomach and respiratory action which is applied at rates of about 200 to about 2,000 g/ha to control undesirable insects.

As used herein, cypermethrin is (RS)-α-cyano-3-phenoxybenzyl(1RS)-cis-trans-3-(2,2-dichlorovinyl)-2,2-dimethylcyclopropanecarboxylate and possesses the following structure:

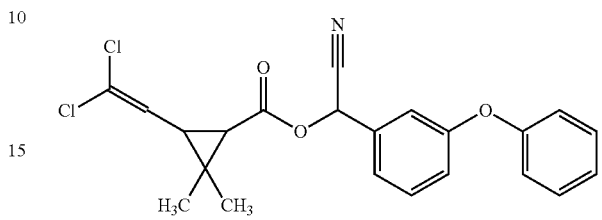

Its insecticidal activity is exemplified in *The Pesticide Manual*, Fifteenth Edition, 2009. Exemplary uses of cypermethrin include its use for the control of Lepidoptera, Coleoptera, Diptera and Homoptera in many crops including rice. Cypermethrin is a non-systemic insecticide with contact and stomach action which is applied at rates of about 10 to about 100 g/ha to control undesirable insects.

As used herein, dimethoate is O,O-dimethyl S-methylcarbamoylmethyl phosphorodithioate and possesses the following structure:

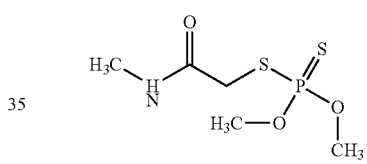

Its insecticidal activity is exemplified in *The Pesticide Manual*, Fifteenth Edition, 2009. Exemplary uses of dimethoate include its use for the control of Lepidoptera, Coleoptera, Diptera, Acari, Aphididae, Aleyrodidae, Coccidae, Collembola, Pseudococcidae and Thysanoptera in a wide variety of crops. Dimethoate is a systemic insecticide with contact and stomach action which is applied at rates of about 80 to about 2,100 g/ha to control undesirable insects.

As used herein, dinotefuran is (EZ)-(RS)-1-methyl-2-nitro-3-(tetrahydro-3-furylmethyl)guanidine and possesses the following structure:

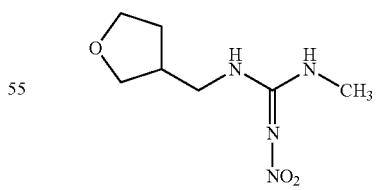

Its insecticidal activity is exemplified in *The Pesticide Manual*, Fifteenth Edition, 2009. Exemplary uses of dinotefuran include its use for the control a range of sucking insects, and Lepidoptera, Coleoptera and Diptera in vegetables, fruit, paddy rice and turf. Dinotefuran is a systemic insecticide with contact and stomach action which is applied at rates of about 100 to about 220 g/ha to control undesirable insects.

As used herein, etofenprox 2-(4-ethoxyphenyl)-2-methylpropyl 3-phenoxybenzyl ether is and possesses the following structure:

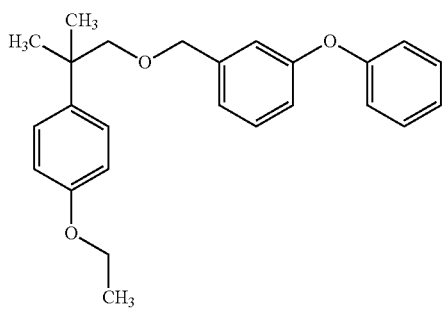 [SMILES: CCOc1ccc(C(C)(C)COCc2cccc(Oc3ccccc3)c2)cc1]

Its insecticidal activity is exemplified in *The Pesticide Manual*, Fifteenth Edition, 2009. Exemplary uses of etofenprox include its use for the control of rice water weevils, skippers, leaf beetles, leafhoppers, planthoppers and bugs in paddy rice. Etofenprox is an insecticide with contact and stomach action which is applied at rates of about 2 to about 8 g/ha to control undesirable insects.

As used herein, fenitrothion is O,O-dimethyl O-(3-methyl-4-nitrophenyl)phosphorothioate and possesses the following structure:

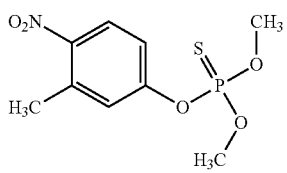

Its insecticidal activity is exemplified in *The Pesticide Manual*, Fifteenth Edition, 2009. Exemplary uses of fenitrothion include its use for the control of chewing, sucking and boring insects in a variety of crops including rice. Fenitrothion is a non-systemic insecticide with contact and stomach action which is applied at rates of about 300 to about 1,200 g/ha to control undesirable insects.

As used herein, fipronil is 5-amino-[2,6-dichloro-4-(trifluoromethyl)phenyl]-4-[(1R,S)-(trifluoromethyl)sulfinyl]-1H-pyrazole-3-carbonitrile and possesses the following structure:

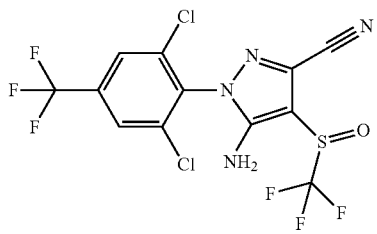 [SMILES: N#Cc1nn(-c2c(Cl)cc(C(F)(F)F)cc2Cl)c(N)c1S(=O)C(F)(F)F]

Its insecticidal activity is exemplified in The Pesticide Manual, Fifteenth Edition, 2009. Exemplary uses of fipronil include its use for the control a variety of insects in many crops, including stem borers, leaf miners, planthoppers, leaf folders/rollers and weevils in rice. Fipronil is a limited systemic insecticide with contact and stomach action which is applied at rates of 10 to 80 g/ha for foliar treatments and from about 100 to about 200 g/ha for soil treatments to control undesirable insects.

As used herein, imidacloprid is (2E)-1-[(6-chloro-3-pyridinyl)methyl]-N-nitro-2-imidazolidinimine and possesses the following structure:

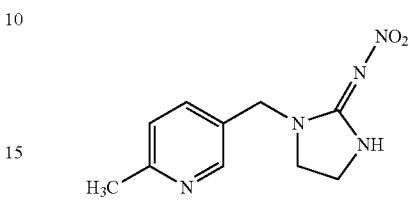

Its insecticidal activity is exemplified in *The Pesticide Manual*, Fifteenth Edition, 2009. Exemplary uses of imidacloprid include its use for the control of sucking and some biting insects such as rice water weevil in a variety of crops including rice. Imidacloprid is a systemic insecticide with contact and stomach action which is applied at rates of about 25 to about 100 g/ha for foliar treatment to control undesirable insects.

As used herein, lambda-cyhalothrin is (R)-cyano(3-phenoxyphenyl)methyl(1S,3S)-rel-3-[(1Z)-2-chloro-3,3,3-trifluoro-1-propen-1-yl]-2,2-dimethylcyclopropanecarboxylate and possesses the following structure:

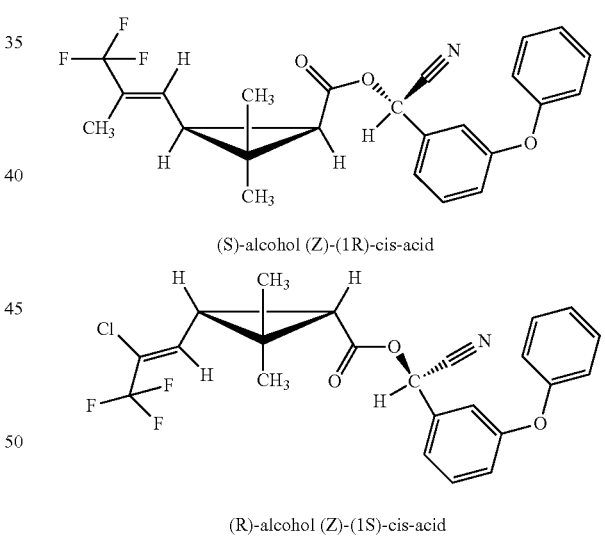

(S)-alcohol (Z)-(1R)-cis-acid (R)-alcohol (Z)-(1S)-cis-acid

Its insecticidal activity is exemplified in *The Pesticide Manual*, Fifteenth Edition, 2009. Exemplary uses of lambda-cyhalothrin include its use for the control of a wide spectrum of insects in a variety of crops. Lambda-cyhalothrin is a non-systemic insecticide with contact and stomach action with rapid knockdown and long residual activity which is applied at rates of about 28 to about 45 g/ha to control undesirable insects in rice.

As used herein, malathion is S-1,2-bis(ethoxycarbonyl)ethyl O,O-dimethyl phosphorodithioate and possesses the following structure:

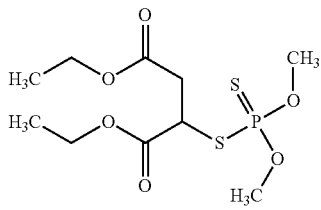

Its insecticidal activity is exemplified in *The Pesticide Manual*, Fifteenth Edition, 2009. Exemplary uses of malathion include its use for the control of Lepidoptera, Coleoptera, Diptera, Hymenoptera and Hemiptera in a wide variety of crops including rice. Malathion is a non-systemic insecticide with contact, stomach and respiratory action which is applied at rates of about 500 to about 1,250 g/ha to control undesirable insects.

As used herein, methamidophos is O,S-dimethyl phosphoramidothioate and possesses the following structure:

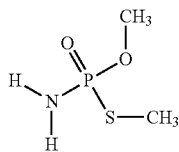

Its insecticidal activity is exemplified in *The Pesticide Manual*, Fifteenth Edition, 2009. Exemplary uses of methamidophos include its use for the control of chewing and sucking insects and spider mites in a wide variety of crops. Methamidophos is a systemic insecticide with contact and stomach action which is applied at rates of about 300 to about 1,200 g/ha to control undesirable insects.

As used herein, piperonyl butoxide is 5-[[2-(2-butoxyethoxy)ethoxy]methyl]-6-propyl-1,3-benzodioxole and possesses the following structure:

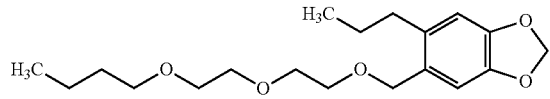 [SMILES: CCCCOCCOCCOCc1cc2c(cc1CCC)OCO2]

Its insecticidal activity is exemplified in The Pesticide Manual, Fifteenth Edition, 2009. Piperonyl butoxide is an insecticide synergist for pyrethrins.

As used herein, pymetrozine is (E)-4,5-dihydro-6-methyl-4-[(3-pyridinyl-methylene)amino]-1,2,4-triazin-3(2H)-one and possesses the following structure:

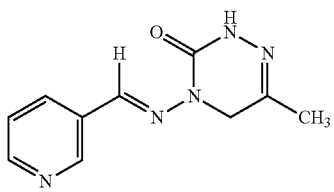 [SMILES: CC1=NNC(=O)N(/N=C/c2cccnc2)C1]

Its insecticidal activity is exemplified in *The Pesticide Manual*, Fifteenth Edition, 2009. Exemplary uses of pymetrozine include its use for the control aphids and whiteflies in a variety of crops. It also controls planthoppers in rice. Pymetrozine is highly selective against Homoptera, causing them to stop feeding. It is applied at rates of about 10 to about 300 g/ha.

As used herein, spinetoram is (2R,3aR,5aR,5bS,9S,13S,14R,16aS,16bR)-2-[(6-deoxy-3-O-ethyl-2,4-di-O-methyl-α-L-mannopyranosyl)oxy]-13-[[(2R,5S,6R)-5-(dimethylamino)-tetrahydro-6-methyl-2H-pyran-2-yl]oxy]-9-ethyl-2,3,3a,4,5,5a,5b,6,9,10,11,12,13,14,16a,16b-hexadecahydro-14-methyl-1H-as-indaceno[3,2-d]oxacyclododecin-7,15-dione mixture with (2S,3aR,5aS,5bS,9S,13S,14R,16aS,16bS)-2-[(6-deoxy-3-O-ethyl-2,4-di-O-methyl-α-L-mannopyranosyl)oxy]-13-[[(2R,5S,6R)-5-(dimethylamino)tetrahydro-6-methyl-2H-pyran-2-yl]oxy]-9-ethyl-2,3,3a,5a,5b,6,9,10,11,12,13,14,16a,16b-tetradecahydro-4,14-dimethyl-1H-as-indaceno[3,2-d]oxacyclododecin-7,15-dione and possesses the following structure:

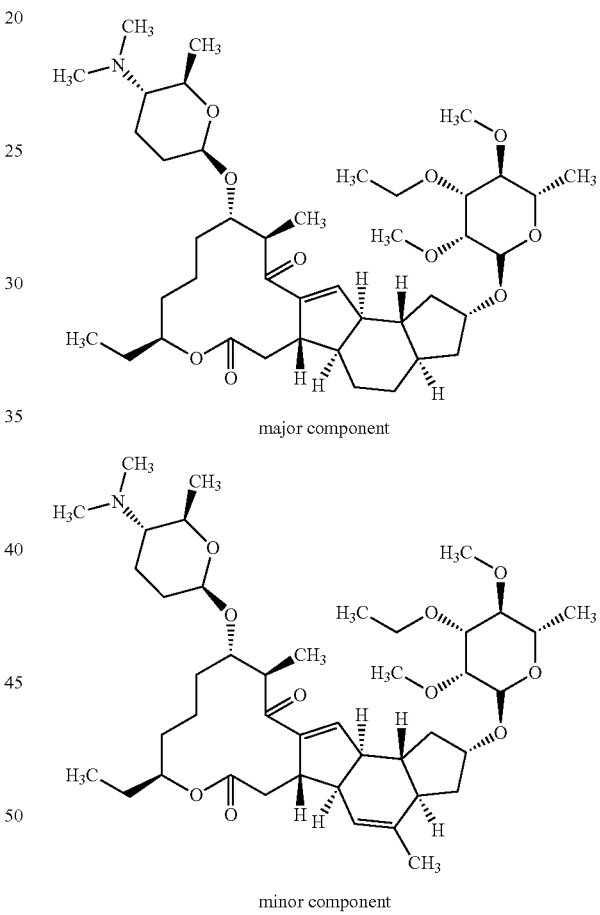

major component minor component

Its insecticidal activity is exemplified in *The Pesticide Manual*, Fifteenth Edition, 2009. Exemplary uses of spinetoram include its use for the control Lepidoptera, Coleoptera, Diptera, Isoptera, Thysanoptera, Orthoptera and certain Homoptera in pome and stone fruit, vines, tree nuts, cotton and vegetables. Spinetoram causes paralysis by contact and ingestion. It is applied at rates of about 10 to about 100 g/ha to control undesirable insects.

As used herein, spinosad is (2R,3aS,5aR,5bS,9S,13S,14R,16aS,16bR)-2-[(6-deoxy-2,3,4-tri-O-methyl-α-L-mannopyranosyl)oxy]-13-[[(2R,5S,6R)-5-(dimethylamino)tetrahydro-6-methyl-2H-pyran-2-yl]oxy]-9-ethyl-2,3,3a,5a,5b,6,9, 10,11,12,13,14,16a,16b-tetradecahydro-14-methyl-1H-as-indaceno[3,2-d]oxacyclododecin-7,15-dione mixture with (2S,3 aR,5aS,5bS,9S,13S,14R,16aS,16bS)-2-[(6-deoxy-2,3,4-tri-O-methyl-α-L-mannopyranosyl)oxy]-13-[[(2R,5S,6R)-5-(dimethylamino)tetrahydro-6-methyl-2H-pyran-2-yl]oxy]-9-ethyl-2,3,3a,5a,5b,6,9,10,11,12,13,14,16a,16b-tetradecahydro-4,14-dimethyl-1H-as-indaceno[3,2-d]oxacyclododecin-7,15-dione and possesses the following structure:

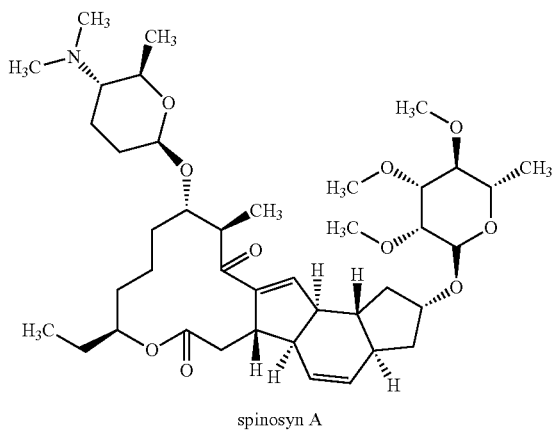

spinosyn A

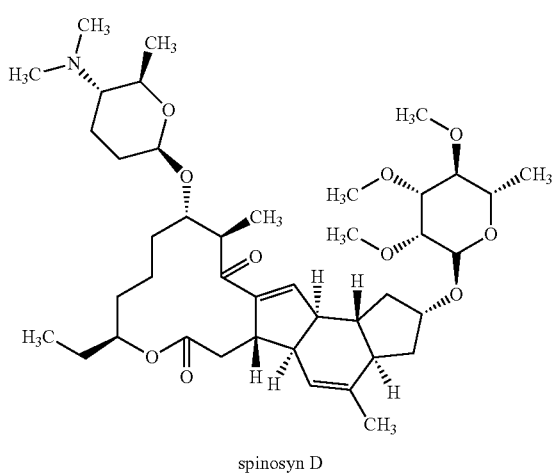

spinosyn D

Its insecticidal activity is exemplified in *The Pesticide Manual*, Fifteenth Edition, 2009. Exemplary uses of spinosad include its use for the control of a broad spectrum of insects in a variety of crops. Spinosad causes paralysis by contact and ingestion. It is applied at rates of about 35 to about 174 g/ha to control undesirable insects.

As used herein, sulfoxaflor is N-[methyloxido[1-[6-(trifluoromethyl)-3-pyridinyl]ethyl]-λ$^4$-sulfanylidene]cyanamide and possesses the following structure:

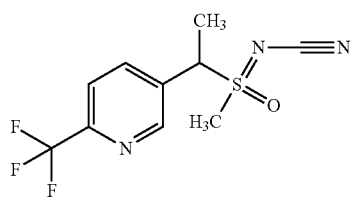 [SMILES: CC(c1ccc(C(F)(F)F)nc1)S(C)(=O)=NC#N]

Its insecticidal activity is exemplified in *The Pesticide Manual*, Fifteenth Edition, 2009. Exemplary uses of sulfoxaflor include its use for the control of a broad spectrum of piercing/sucking insects, including species that are difficult to control, in a variety of crops. It also controls planthoppers in rice. Sulfoxaflor is a systemic insecticide with contact and stomach action which is applied at rates of about 12 to about 150 g/ha to control undesirable insects.

As used herein, triazophos is O,O-diethyl O-1-phenyl-1H-1,2,4-triazol-3-yl phosphorothioate and possesses the following structure:

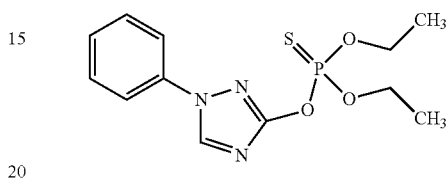

Its insecticidal activity is exemplified in *The Pesticide Manual*, Fifteenth Edition, 2009. Exemplary uses of triazophos include its use for the control of stem borers, leaf folders, leaf hoppers and planthoppers in rice. Triazophos is a non-systemic insecticide with contact and stomach action which is applied at rates of about 600 g/ha to control undesirable insects.

As used herein, herbicide means a compound, e.g., active ingredient that kills, controls or otherwise adversely modifies the growth of undesirable vegetation when applied in an appropriate amount. As used herein, insecticide means a compound, e.g., active ingredient that kills, controls or otherwise adversely modifies the growth of insects.

As used herein, an insecticidally effective or controlling amount is an amount of active ingredient which causes an adversely modifying effect to the insects to be controlled, e.g., causing deviations from natural development, killing, effecting regulation, causing desiccation, causing retardation, and the like.

As used herein, a herbicidally effective or controlling amount is an amount of active ingredient which causes an adversely modifying effect to the undesirable vegetation, e.g., causing deviations from natural development, killing, effecting regulation, causing desiccation, causing retardation, and the like.

As used herein, controlling undesirable vegetation means preventing, reducing, killing, or otherwise adversely modifying the development of plants and vegetation. Described herein are methods of controlling undesirable vegetation through the application of certain herbicide and insecticide combinations or compositions. Methods of application include, but are not limited to applications to the vegetation or locus thereof, e.g., application to the area adjacent to the vegetation, as well as pre-emergence, post-emergence, foliar (broadcast, directed, banded, spot, mechanical, over-the-top, or rescue), and in-water applications (emerged and submerged vegetation, broadcast, spot, mechanical, water-injected, granular broadcast, granular spot, shaker bottle, or stream spray) via hand, backpack, machine, tractor, or aerial (airplane and helicopter) application methods.

As used herein, plants and vegetation include, but are not limited to, germinant seeds, emerging seedlings, plants emerging from vegetative propagules, immature vegetation, and established vegetation.

As used herein, agriculturally acceptable salts and esters refer to salts and esters that exhibit herbicidal activity, or that are or can be converted in plants, water, or soil to the referenced herbicide. Exemplary agriculturally acceptable esters are those that are or can be hydrolyzed, oxidized, metabolized, or otherwise converted, e.g., in plants, water, or soil, to the corresponding carboxylic acid which, depending on the pH, may be in the dissociated or undissociated form.

Exemplary salts include those derived from alkali or alkaline earth metals and those derived from ammonia and amines. Exemplary cations include sodium, potassium, magnesium, and ammonium cations of the formula:

$$R^1R^2R^3R^4N^+$$

wherein $R^1$, $R^2$, $R^3$ and $R^4$ each, independently represents hydrogen or $C_1$-$C_{12}$ alkyl, $C_3$-$C_{12}$ alkenyl or $C_3$-$C_{12}$ alkynyl, each of which is optionally substituted by one or more hydroxy, $C_1$-$C_4$ alkoxy, $C_1$-$C_4$ alkylthio or phenyl groups, provided that $R^1$, $R^2$, $R^3$ and $R^4$ are sterically compatible. Additionally, any two of $R^1$, $R^2$, $R^3$ and $R^4$ together may represent an aliphatic difunctional moiety containing one to twelve carbon atoms and up to two oxygen or sulfur atoms. Salts can be prepared by treatment with a metal hydroxide, such as sodium hydroxide, with an amine, such as ammonia, trimethylamine, diethanolamine, 2-methylthiopropylamine, bisallylamine, 2-butoxyethylamine, morpholine, cyclododecylamine, or benzylamine or with a tetraalkylammonium hydroxide, such as tetramethylammonium hydroxide or choline hydroxide.

Exemplary esters include those derived from $C_1$-$C_{12}$ alkyl, $C_3$-$C_{12}$ alkenyl, $C_3$-$C_{12}$ alkynyl or $C_2$-$C_{10}$ aryl-substituted alkyl alcohols, such as methyl alcohol, isopropyl alcohol, 1-butanol, 2-ethylhexanol, butoxyethanol, methoxypropanol, allyl alcohol, propargyl alcohol, cyclohexanol or unsubstituted or substituted benzyl alcohols. Benzyl alcohols may be substituted with from 1-3 substituents independently selected from halogen, $C_1$-$C_4$ alkyl or $C_1$-$C_4$ alkoxy. Esters can be prepared by coupling of the acids with the alcohol using any number of suitable activating agents such as those used for peptide couplings such as dicyclohexylcarbodiimide (DCC) or carbonyl diimidazole (CDI); by reacting the acids with alkylating agents such as alkylhalides or alkylsulfonates in the presence of a base such as triethylamine or lithium carbonate; by reacting the corresponding acid chloride of an acid with an appropriate alcohol; by reacting the corresponding acid with an appropriate alcohol in the presence of an acid catalyst or by transesterification.

Compositions and Methods

Provided herein are herbicidal compositions comprising a herbicidally effective amount of (a) a compound of the formula (I)

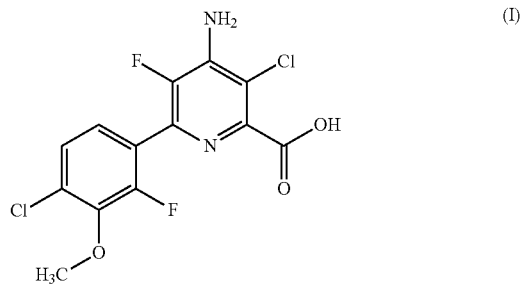 [SMILES: "(I)" ; COc1c(Cl)ccc(-c2nc(C(=O)O)c(Cl)c(N)c2F)c1F]

or an agriculturally acceptable salt or ester of thereof, and (b) insecticides.

Provided herein are also methods of controlling undesirable vegetation comprising contacting the vegetation or locus thereof, i.e., the area adjacent to the vegetation with or applying to the soil or water to prevent the emergence or growth of vegetation a herbicidally effective amount of the compound of formula (I) or agriculturally acceptable salt or ester thereof and (b) insecticides, including but not limited to, acephate, carbaryl, carbofuran, cartap, chlorpyrifos, cypermethrin, dimethoate, dinotefuran, etofenprox, fenitrothion, fipronil, imidacloprid, lambda-cyhalothrin, malathion, methamidophos, piperonyl butoxide, pymetrozine, spinetoram, spinosad, sulfoxaflor and triazophos. In certain embodiments, the methods employ the compositions described herein.

Furthermore, in some embodiments, the combination of compound (I) or agriculturally acceptable salt or ester thereof and acephate, carbaryl, carbofuran, cartap, chlorpyrifos, cypermethrin, dimethoate, dinotefuran, etofenprox, fenitrothion, fipronil, imidacloprid, lambda-cyhalothrin, malathion, methamidophos, piperonyl butoxide, pymetrozine, spinetoram, spinosad, sulfoxaflor or triazophos exhibits synergism, e.g., the herbicidal activity is more effective in combination than when compound of formula (I) is applied individually. Synergism has been defined as "an interaction of two or more factors such that the effect when combined is greater than the predicted effect based on the response of each factor applied separately." Senseman, S., Ed. Herbicide Handbook. $9^{th}$ ed. Lawrence: Weed Science Society of America, 2007. In certain embodiments, the compositions exhibit synergy as determined by the Colby's equation (Colby, S. R. Calculation of the synergistic and antagonistic response of herbicide combinations. *Weeds* 1967, 15, 20-22.

In certain embodiments of the compositions and methods described herein, the compound of formula (I), i.e., the carboxylic acid, is employed. In certain embodiments, a carboxylate salt of the compound of formula (I) is employed. In certain embodiments, an aralkyl or alkyl ester is employed. In certain embodiments, a benzyl, substituted benzyl, or $C_{1-4}$ alkyl, e.g., n-butyl ester is employed. In certain embodiments, the benzyl ester is employed.

In some embodiments, the compound of formula (I) or salt or ester thereof and acephate, carbaryl, carbofuran, cartap, chlorpyrifos, cypermethrin, dimethoate, dinotefuran, etofenprox, fenitrothion, fipronil, imidacloprid, lambda-cyhalothrin, malathion, methamidophos, pymetrozine, spinetoram, spinosad, sulfoxaflor or triazophos are formulated in one composition, tank-mixed, applied simultaneously, or applied sequentially.

Herbicidal activity is exhibited by the compounds when they are applied directly to the plant or to the area adjacent to the plant at any stage of growth. The effect observed depends upon the plant species to be controlled, the stage of growth of the plant, the application parameters of dilution and spray drop size, the particle size of solid components, the environmental conditions at the time of use, the specific compound employed, the specific adjuvants and carriers employed, the soil type, and the like, as well as the amount of chemical applied. These and other factors can be adjusted to promote non-selective or selective herbicidal action. In some embodiments, the compositions described herein are applied as a post-emergence application, pre-emergence application, or in-water application to flooded paddy rice or water bodies (e.g., ponds, lakes and streams), to relatively immature undesirable vegetation to achieve the maximum control of weeds.

In some embodiments, the compositions and methods provided herein are utilized to control weeds in crops, including but not limited to direct-seeded, water-seeded and transplanted rice, cereals, wheat, barley, oats, rye, *sorghum*, corn/ maize, sugarcane, sunflower, oilseed rape, canola, sugar beet, soybean, cotton, pineapple, pastures, grasslands, rangelands, fallowland, turf, tree and vine orchards, plantation crops, vegetables, industrial vegetation management (IVM) and rights-of-way (ROW).

In certain embodiments, the compositions and methods provided herein are utilized to control weeds in rice. In certain embodiments, the rice is direct-seeded, water-seeded, or transplanted rice.

The compositions and methods described herein may be used to control undesirable vegetation in glyphosate-tolerant-, 5-enolpyruvylshikimate-3-phosphate (EPSP) synthase inhibitor-tolerant-, glufosinate-tolerant-, glutamine synthetase inhibitor-tolerant-, dicamba-tolerant-, phenoxy auxin-tolerant-, pyridyloxy auxin-tolerant-, auxin-tolerant-, auxin transport inhibitor-tolerant-, aryloxyphenoxypropionate-tolerant-, cyclohexanedione-tolerant-, phenylpyrazoline-tolerant-, acetyl CoA carboxylase (ACCase) inhibitor-tolerant-, imidazolinone-tolerant-, sulfonylurea-tolerant-, pyrimidinylthiobenzoate-tolerant-, triazolopyrimidine-tolerant-, sulfonylaminocarbonyltriazolinone-tolerant-, acetolactate synthase (ALS) or acetohydroxy acid synthase (AHAS) inhibitor-tolerant-, 4-hydroxyphenyl-pyruvate dioxygenase (HPPD) inhibitor-tolerant-, phytoene desaturase inhibitor-tolerant-, carotenoid biosynthesis inhibitor-tolerant-, protoporphyrinogen oxidase (PPO) inhibitor-tolerant-, cellulose biosynthesis inhibitor-tolerant-, mitosis inhibitor-tolerant-, microtubule inhibitor-tolerant-, very long chain fatty acid inhibitor-tolerant-, fatty acid and lipid biosynthesis inhibitor-tolerant-, photosystem I inhibitor-tolerant-, photosystem II inhibitor-tolerant-, triazine-tolerant- and bromoxynil-tolerant-crops (such as, but not limited to, soybean, cotton, canola/oilseed rape, rice, cereals, corn, sorghum, sunflower, sugar beet, sugarcane, turf, etc.), for example, in conjunction with glyphosate, EPSP synthase inhibitors, glufosinate, glutamine synthase inhibitors, dicamba, phenoxy auxins, pyridyloxy auxins, synthetic auxins, auxin transport inhibitors, aryloxyphenoxypropionates, cyclohexanediones, phenylpyrazolines, ACCase inhibitors, imidazolinones, sulfonylureas, pyrimidinylthiobenzoates, triazolopyrimidines, sulfonylaminocarbonyltriazolinones, ALS or AHAS inhibitors, HPPD inhibitors, phytoene desaturase inhibitors, carotenoid biosynthesis inhibitors, PPO inhibitors, cellulose biosynthesis inhibitors, mitosis inhibitors, microtubule inhibitors, very long chain fatty acid inhibitors, fatty acid and lipid biosynthesis inhibitors, photosystem I inhibitors, photosystem II inhibitors, triazines, and bromoxynil. The compositions and methods may be used in controlling undesirable vegetation in crops possessing multiple or stacked traits conferring tolerance to multiple chemistries and/or inhibitors of multiple modes-of-action. In some embodiments, the compound of formula (I) or salt or ester thereof and complementary herbicide or salt or ester thereof are used in combination with herbicides that are selective for the crop being treated and which complement the spectrum of weeds controlled by these compounds at the application rate employed. In some embodiments, the compositions described herein and other complementary herbicides are applied at the same time, either as a combination formulation, as a tank mix, or sequentially.

The compositions and methods may be used in controlling undesirable vegetation in crops possessing agronomic stress tolerance (including but not limited to drought, cold, heat, salt, water, nutrient, fertility, pH), pest tolerance (including but not limited to insects, fungi and pathogens) and crop improvement traits (including but not limited to yield; protein, carbohydrate, or oil content; protein, carbohydrate, or oil composition; plant stature and plant architecture).

The compositions and methods provided herein are utilized to control undesirable vegetation. Undesirable vegetation includes, but is not limited to, undesirable vegetation that occurs in direct-seeded, water-seeded and transplanted rice, cereals, wheat, barley, oats, rye, sorghum, corn/maize, sugarcane, sunflower, oilseed rape, canola, sugar beet, soybean, cotton, pineapple, pastures, grasslands, rangelands, fallowland, turf, tree and vine orchards, plantation crops, vegetables, aquatics, industrial vegetation management (IVM) and rights-of-way ROW).

In some embodiments, the methods provided herein are utilized to control undesirable vegetation in rice. In certain embodiments, the undesirable vegetation is *Brachiaria platyphylla* (Groseb.) Nash or *Urochloa platyphylla* (Nash) R. D. Webster (broadleaf signalgrass, BRAPP), *Digitaria sanguinalis* (L.) Scop. (large crabgrass, DIGSA), *Echinochloa* species (ECHSS), *Echinochloa crus-galli* (L.) P. Beauv. (barnyardgrass, ECHCG), *Echinochloa crus-pavonis* (Kunth) Schult. (gulf cockspur, ECHCV), *Echinochloa colonum* (L.) LINK (junglerice, ECHCO), *Echinochloa oryzoides* (Ard.) Fritsch (early watergrass, ECHOR), *Echinochloa oryzicola* (Vasinger) Vasinger (late watergrass, ECHPH), *Echinochloa phyllopogon* (Stapf) Koso-Pol. (rice barnyardgrass, ECHPH), *Echinochloa polystachya* (Kunth) Hitchc. (creeping river grass, ECHPO), *Ischaemum rugosum* Salisb. (saramollagrass, ISCRU), *Leptochloa chinensis* (L.) Nees (Chinese sprangletop, LEFCH), *Leptochloa fascicularis* (Lam.) Gray (bearded sprangletop, LEFFA), *Leptochloa panicoides* (Presl.) Hitchc. (Amazon sprangletop, LEFPA), *Oryza* species (red and weedy rice, ORYSS), *Panicum dichotomiflorum* (L.) Michx. (fall *panicum*, PANDI), *Paspalum dilatatum* Poir. (dallisgrass, PASDI), *Rottboellia cochinchinensis* (Lour.) W. D. Clayton (itchgrass, ROOEX), *Cyperus* species (CYPSS), *Cyperus difformis* L. (smallflower flatsedge, CYPDI), *Cyperus dubius* Rottb. (MAPDU), *Cyperus esculentus* L. (yellow nutsedge, CYPES), *Cyperus iria* L. (rice flatsedge, CYPIR), *Cyperus rotundus* L. (purple nutsedge, CYPRO), *Cyperus serotinus* Rottb./C. B. Clarke (tidalmarsh flatsedge, CYPSE), *Eleocharis* species (ELOSS), *Fimbristylis miliacea* (L.) Vahl (globe fringerush, FIMMI), *Schoenoplectus* species (SCPSS), *Schoenoplectus juncoides* Roxb. (Japanese bulrush, SCPJU), *Bolboschoenus maritimus* (L.) Palla or *Schoenoplectus maritimus* L. Lye (sea clubrush, SCPMA), *Schoenoplectus mucronatus* L. (ricefield bulrush, SCPMU), *Aeschynomene* species, (jointvetch, AESSS), *Alternanthera philoxeroides* (Mart.) Griseb. (alligatorweed, ALRPH), *Alisma plantago-aquatica* L. (common waterplantain, ALSPA), *Amaranthus* species, (pigweeds and amaranths, AMASS), *Ammannia coccinea* Rottb. (redstem, AMMCO), *Commelina benghalensis* L. (Benghal dayflower, COMBE), *Eclipta alba* (L.) Hassk. (American false daisy, ECLAL), *Heteranthera limosa* (SW.) Willd./Vahl (ducksalad, HETLI), *Heteranthera reniformis* R. & P. (roundleaf mudplantain, HETRE), *Ipomoea* species (morningglories, IPOSS), *Ipomoea hederacea* (L.) Jacq. (ivyleaf morningglory, IPOHE), *Lindernia dubia* (L.) Pennell (low false pimpernel, LIDDU), *Ludwigia* species (LUDSS), *Ludwigia linifolia* Poir. (southeastern primrose-willow, LUDLI), *Ludwigia octovalvis* (Jacq.) Raven (longfruited primrose-willow, LUDOC), *Monochoria korsakowii* Regel & Maack (*monochoria*, MOOKA), *Monochoria vaginalis* (Burm. F.) C. Presl ex Kuhth, (*monochoria*, MOOVA), *Murdannia nudiflora* (L.) Brenan (doveweed, MUDNU), *Polygonum pensylvanicum* L., (Pennsylvania smartweed, POLPY), *Polygonum persicaria* L. (ladysthumb, POLPE), *Polygonum hydropiperoides* Michx. (mild smartweed, POLHP), *Rotala indica* (Willd.) Koehne (Indian toothcup, ROTIN), *Sagittaria* species, (arrowhead, SAGSS), *Sesbania exaltata* (Raf.) Cory/Rydb. Ex Hill (hemp *sesbania*, SEBEX), or *Sphenoclea zeylanica* Gaertn. (gooseweed, SPDZE).

In some embodiments, the methods provided herein are utilized to control undesirable vegetation in cereals. In certain embodiments, the undesirable vegetation is *Alopecurus myosuroides* Huds. (blackgrass, ALOMY), *Apera spica-venti* (L.) Beauv. (windgrass, APESV), *Avena fatua* L. (wild oat, AVEFA), *Bromus tectorum* L. (downy brome, BROTE), *Lolium multiflorum* Lam. (Italian ryegrass, LOLMU), *Phalaris minor* Retz. (littleseed canarygrass, PHAMI), *Poa annua* L. (annual bluegrass, POAAN), *Setaria pumila* (Poir.) Roemer & J. A. Schultes (yellow foxtail, SETLU), *Setaria viridis* (L.) Beauv. (green foxtail, SETVI), *Amaranthus retroflexus* L. (redroot pigweed, AMARE), *Brassica* species (BRSSS), *Chenopodium album* L. (common lambsquarters, CHEAL), *Cirsium arvense* (L.) Scop. (Canada thistle, CIRAR), *Galium aparine* L. (catchweed bedstraw, GALAP), *Kochia scoparia* (L.) Schrad. (*kochia*, KCHSC), *Lamium purpureum* L. (purple deadnettle, LAMPU), *Matricaria recutita* L. (wild chamomile, MATCH), *Matricaria matricarioides* (Less.) Porter (pineappleweed, MATMT), *Papaver rhoeas* L. (common poppy, PAPRH), *Polygonum convolvulus* L. (wild buckwheat, POLCO), *Salsola tragus* L. (Russian thistle, SASKR), *Sinapis* species (SINSS), *Sinapis arvensis* L. (wild mustard, SINAR), *Stellaria media* (L.) Vill. (common chickweed, STEME), *Veronica persica* Poir. (Persian speedwell, VERPE), *Viola arvensis* Murr. (field violet, VIOAR), or *Viola tricolor* L. (wild violet, VIOTR).

In some embodiments, the methods provided herein are utilized to control undesirable vegetation in range and pasture, fallowland, IVM and ROW. In certain embodiments, the undesirable vegetation is *Ambrosia artemisiifolia* L. (common ragweed, AMBEL), *Cassia obtusifolia* (sickle pod, CASOB), *Centaurea maculosa* auct. non Lam. (spotted knapweed, CENMA), *Cirsium arvense* (L.) Scop. (Canada thistle, CIRAR), *Convolvulus arvensis* L. (field bindweed, CONAR), *Daucus carota* L. (wild carrot, DAUCA), *Euphorbia esula* L. (leafy spurge, EPHES), *Lactuca serriola* L./Torn. (prickly lettuce, LACSE), *Plantago lanceolata* L. (buckhorn plantain, PLALA), *Rumex obtusifolius* L. (broadleaf dock, RUMOB), *Sida spinosa* L. (prickly *sida*, SIDSP), *Sinapis arvensis* L. (wild mustard, SINAR), *Sonchus arvensis* L. (perennial sowthistle, SONAR), *Solidago* species (goldenrod, SOOSS), *Taraxacum officinale* G. H. Weber ex Wiggers (dandelion, TAROF), *Trifolium repens* L. (white clover, TRFRE), or *Urtica dioica* L. (common nettle, URTDI).

In some embodiments, the methods provided herein are utilized to control undesirable vegetation found in row crops, tree and vine crops, and perennial crops. In certain embodiments, the undesirable vegetation is *Alopecurus myosuroides* Huds. (blackgrass, ALOMY), *Avena fatua* L. (wild oat, AVEFA), *Brachiaria decumbens* Stapf. or *Urochloa decumbens* (Stapf) R. D. Webster (Surinam grass, BRADC), *Brachiaria brizantha* (Hochst. ex A. Rich.) Stapf. or *Urochloa brizantha* (Hochst. ex A. Rich.) R. D. (beard grass, BRABR), *Brachiaria platyphylla* (Groseb.) Nash or *Urochloa platyphylla* (Nash) R. D. Webster (broadleaf signalgrass, BRAPP), *Brachiaria plantaginea* (Link) Hitchc. or *Urochloa plantaginea* (Link) R. D. Webster (alexandergrass, BRAPL), *Cenchrus echinatus* L. (southern sandbur, CENEC), *Digitaria horizontalis* Willd. (Jamaican crabgrass, DIGHO), *Digitaria insularis* (L.) Mez ex Ekman (sourgrass, TRCIN), *Digitaria sanguinalis* (L.) Scop. (large crabgrass, DIGSA), *Echinochloa crus-galli* (L.) P. Beauv. (barnyardgrass, ECHCG), *Echinochloa colonum* (L.) Link (junglerice, ECHCO), *Eleusine indica* (L.) Gaertn. (goosegrass, ELEIN), *Lolium multiflorum* Lam. (Italian ryegrass, LOLMU), *Panicum dichotomiflorum* Michx. (fall *panicum*, PANDI), *Panicum miliaceum* L. (wild-proso millet, PANMI), *Setaria faberi* Herrm. (giant foxtail, SETFA), *Setaria viridis* (L.) Beauv. (green foxtail, SETVI), *Sorghum halepense* (L.) Pers. (Johnsongrass, SORHA), *Sorghum bicolor* (L.) Moench ssp. *Arundinaceum* (shattercane, SORVU), *Cyperus esculentus* L. (yellow nutsedge, CYPES), *Cyperus rotundus* L. (purple nutsedge, CYPRO), *Abutilon theophrasti* Medik. (velvetleaf, ABUTH), *Amaranthus* species (pigweeds and amaranths, AMASS), *Ambrosia artemisiifolia* L. (common ragweed, AMBEL), *Ambrosia psilostachya* DC. (western ragweed, AMBPS), *Ambrosia trifida* L. (giant ragweed, AMBTR), *Anoda cristata* (L.) Schlecht. (spurred *anoda*, ANVCR), *Asclepias syriaca* L. (common milkweed, ASCSY), *Bidens pilosa* L. (hairy beggarticks, BIDPI), *Borreria* species (BOISS), *Borreria alata* (Aubl.) DC. or *Spermacoce alata* Aubl. (broadleaf buttonweed, BOILF), *Spermacose latifolia* (broadleaved buttonweed, BOILF), *Chenopodium album* L. (common lambsquarters, CHEAL), *Cirsium arvense* (L.) Scop. (Canada thistle, CIRAR), *Commelina benghalensis* L. (tropical spiderwort, COMBE), *Datura stramonium* L. (jimsonweed, DATST), *Daucus carota* L. (wild carrot, DAUCA), *Euphorbia heterophylla* L. (wild poinsettia, EPHHL), *Euphorbia hirta* L. or Chamaesyce *hirta* (L.) Millsp. (garden spurge, EPHHI), *Euphorbia dentata* Michx. (toothed spurge, EPHDE), *Erigeron bonariensis* L. or *Conyza bonariensis* (L.) Cronq. (hairy fleabane, ERIBO), *Erigeron canadensis* L. or *Conyza canadensis* (L.) Cronq. (Canadian fleabane, ERICA), *Conyza sumatrensis* (Retz.) E. H. Walker (tall fleabane, ERIFL), *Helianthus annuus* L. (common sunflower, HELAN), *Jacquemontia tamnifolia* (L.) Griseb. (smallflower morningglory, IAQTA), *Ipomoea hederacea* (L.) Jacq. (ivyleaf morningglory, IPOHE), *Ipomoea lacunosa* L. (white morningglory, IPOLA), *Lactuca serriola* L./Torn. (prickly lettuce, LACSE), *Portulaca oleracea* L. (common purslane, POROL), *Richardia* species (pusley, RCHSS), *Sida* species (*sida*, SIDSS), *Sida spinosa* L. (prickly *sida*, SIDSP), *Sinapis arvensis* L. (wild mustard, SINAR), *Solanum ptychanthum* Dunal (eastern black nightshade, SOLPT), *Tridax procumbens* L. (coat buttons, TRQPR), or *Xanthium strumarium* L. (common cocklebur, XANST).

In some embodiments, the methods provided herein are utilized to control undesirable vegetation in turf. In certain embodiments, the undesirable vegetation is *Bellis perennis* L. (English daisy, BELPE), *Cyperus esculentus* L. (yellow nutsedge, CYPES), *Cyperus* species (CYPSS), *Digitaria sanguinalis* (L.) Scop. (large crabgrass, DIGSA), *Diodia virginiana* L. (Virginia buttonweed, DIQVI), *Euphorbia* species (spurge, EPHSS), *Glechoma hederacea* L. (ground ivy, GLEHE), *Hydrocotyle umbellata* L. (dollarweed, HYDUM), *Kyllinga* species (kylling a, KYLSS), *Lamium amplexicaule* L. (henbit, LAMAM), *Murdannia nudiflora* (L.) Brenan (doveweed, MUDNU), *Oxalis* species (woodsorrel, OXASS), *Plantago major* L. (broadleaf plantain, PLAMA), *Plantago lanceolata* L. (buckhorn/narrowleaf plantain, PLALA), *Phyllanthus urinaria* L. (chamberbitter, PYLTE), *Rumex obtusifolius* L. (broadleaf dock, RUMOB), *Stachys floridana* Shuttlew. (Florida betony, STAFL), *Stellaria media* (L.) Vill. (common chickweed, STEME), *Taraxacum officinale* G. H. Weber ex Wiggers (dandelion, TAROF), *Trifolium repens* L. (white clover, TRFRE), or *Viola* species (wild violet, VIOSS).

In some embodiments, the compositions and methods provided herein are utilized to control undesirable vegetation consisting of grass, broadleaf and sedge weeds. In certain embodiments, the compositions and methods provided herein are utilized to control undesirable grass, broadleaf and sedge vegetation including but not limited to *Brachiaria* or *Urochloa, Bolboschoenus, Cyperus, Digitaria, Echinochloa, Ipomoea, Leptochloa* and *Schoenoplectus*.

In some embodiments, the combination of compound (I) or agriculturally acceptable ester or salt thereof and insecticides are used to control, including but not limited to broadleaf signalgrass (*Brachiaria platyphylla* or *Urochloa platyphylla*), yellow nutsedge (*Cyperus esculentus*), rice flatsedge (*Cyperus iria*), purple nutsedge, (*Cyperus rotundus*), large crabgrass (*Digitaria sanguinalis*), barnyardgrass (*Echinochloa crus-galli*), junglerice (*Echinochloa colona*), ivyleaf morningglory (*Ipomoea hederacea*), Chinese sprangletop (*Leptochloa chinensis*), bearded sprangletop (*Leptochloa fascicularis*), Amazon sprangletop (*Leptochloa panicoides*), sea clubrush (*Schoenoplectus maritimus* or *Bolboschoenus maritimus*) and Japanese bulrush (*Schoenoplectus juncoides*).

The compounds of formula I or agriculturally acceptable salt or ester thereof may be used to control herbicide resistant or tolerant weeds. The methods employing the combination of a compound of formula I or agriculturally acceptable salt or ester thereof and the compositions described herein may also be employed to control herbicide resistant or tolerant weeds. Exemplary resistant or tolerant weeds include, but are not limited to, biotypes resistant or tolerant to acetolactate synthase (ALS) or acetohydroxy acid synthase (AHAS) inhibitors (e.g., imidazolinones, sulfonylureas, pyrimidinylthiobenzoates, triazolopyrimidines, sulfonylaminocarbonyltriazolinones), photosystem II inhibitors (e.g., phenylcarbamates, pyridazinones, triazines, triazinones, uracils, amides, ureas, benzothiadiazinones, nitriles, phenylpyridazines), acetyl CoA carboxylase (ACCase) inhibitors (e.g., aryloxyphenoxypropionates, cyclohexanediones, phenylpyrazolines), synthetic auxins (e.g., benzoic acids, phenoxycarboxylic acids, pyridine carboxylic acids, quinoline carboxylic acids), auxin transport inhibitors (e.g., phthalamates, semicarbazones), photosystem I inhibitors (e.g., bipyridyliums), 5-enolpyruvylshikimate-3-phosphate (EPSP) synthase inhibitors (e.g., glyphosate), glutamine synthetase inhibitors (e.g., glufosinate, bialafos), microtubule assembly inhibitors (e.g., benzamides, benzoic acids, dinitroanilines, phosphoramidates, pyridines), mitosis inhibitors (e.g., carbamates), very long chain fatty acid (VLCFA) inhibitors (e.g., acetamides, chloroacetamides, oxyacetamides, tetrazolinones), fatty acid and lipid synthesis inhibitors (e.g., phosphorodithioates, thiocarbamates, benzofuranes, chlorocarbonic acids), protoporphyrinogen oxidase (PPO) inhibitors (e.g., diphenylethers, N-phenylphthalimides, oxadiazoles, oxazolidinediones, phenylpyrazoles, pyrimidindiones, thiadiazoles, triazolinones), carotenoid biosynthesis inhibitors (e.g., clomazone, amitrole, aclonifen), phytoene desaturase (PDS) inhibitors (e.g., amides, anilidex, furanones, phenoxybutan-amides, pyridiazinones, pyridines), 4-hydroxyphenyl-pyruvate-dioxygenase (HPPD) inhibitors (e.g., callistemones, isoxazoles, pyrazoles, triketones), cellulose biosynthesis inhibitors (e.g., nitriles, benzamides, quinclorac, triazolocarboxamides), herbicides with multiple modes-of-action such as quinclorac, and unclassified herbicides such as arylaminopropionic acids, difenzoquat, endothall, and organoarsenicals. Exemplary resistant or tolerant weeds include, but are not limited to, biotypes with resistance or tolerance to multiple herbicides, biotypes with resistance or tolerance to multiple chemical classes, biotypes with resistance or tolerance to multiple herbicide modes-of-action, and biotypes with multiple resistance or tolerance mechanisms (e.g., target site resistance or metabolic resistance).

In certain embodiments of the compositions and methods described herein, the compound of formula (I) or salt or ester thereof is used in combination with acephate. With respect to the compositions, in some embodiments, the weight ratio of the compound of formula (I) or salt or ester thereof to acephate is within the range of from about 1:1000 to about 6:1. In certain embodiments, the weight ratio of the compound of formula (I) or salt or ester thereof to acephate is within the range of from about 1:70 to about 1:5.

With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 52 grams active ingredient per hectare (g ai/ha) to about 2,300 g ai/ha based on the total amount of active ingredients in the composition. In certain embodiments, the composition is applied at an application rate of from about 148 grams active ingredient per hectare (g ai/ha) to about 592 g ai/ha based on the total amount of active ingredients in the composition.

In some embodiments, the methods comprise contacting the undesirable vegetation or locus thereof or applying to the soil or water to prevent the emergence or growth of vegetation with a compound of formula (I) or salt or ester thereof and acephate, e.g., sequentially or simultaneously. In some embodiments, acephate is applied at a rate from about 50 g ai/ha to about 2,000 g ai/ha and the compound of formula (I) or salt or ester thereof is applied at a rate of about 2 g ae/ha to about 300 g ae/ha. In some embodiments, acephate is applied at a rate from about 140 g ai/ha to about 560 g ai/ha and the compound of formula (I) or salt or ester thereof is applied at a rate from about 8 g acid equivalent per hectare (g ae/ha) to about 32 g ae/ha. In certain embodiments, the methods utilize the compound of formula (I), or its benzyl ester and acephate. In one embodiment, the methods utilize the compound of formula (I) and acephate, wherein the compound of formula (I) is applied at a rate of from about 8 g acid equivalent per hectare (g ae/ha) to about 32 g ae/ha, and acephate is applied at a rate of about 140 g ai/ha to about 560 g ai/ha. In one embodiment, the methods utilize the benzyl ester of the compound of formula (I) and acephate, wherein the benzyl ester of the compound of formula (I) is applied at a rate of from about 8 g acid equivalent per hectare (g ae/ha) to about 32 g ae/ha, and acephate is applied at a rate of about 140 g ai/ha to about 560 g ai/ha.

In certain embodiments of the compositions and methods described herein, the compound of formula (I) or salt or ester thereof is used in combination with carbaryl. With respect to the compositions, in some embodiments, the weight ratio of the compound of formula (I) or salt or ester thereof to carbaryl is within the range of from about 1:500 to about 150:1. In certain embodiments, the weight ratio of the compound of formula (I) or salt or ester thereof to carbaryl is within the range of from about 1:22 to about 107:1.

With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 4 grams active ingredient per hectare (g ai/ha) to about 1,300 g ai/ha based on the total amount of active ingredients in the composition. In certain embodiments, the composition is applied at an application rate of from about 7 grams active ingredient per hectare (g ai/ha) to about 115 g ai/ha based on the total amount of active ingredients in the composition.

In some embodiments, the methods comprise contacting the undesirable vegetation or locus thereof or applying to the soil or water to prevent the emergence or growth of vegetation with a compound of formula (I) or salt or ester thereof and carbaryl, e.g., sequentially or simultaneously. In some embodiments, carbaryl is applied at a rate from about 2 g ai/ha to about 1,000 g ai/ha and the compound of formula (I) or salt or ester thereof is applied at a rate from about 2 g ae/ha to about 300 g ae/ha. In some embodiments, carbaryl is applied at a rate from about 3 g ai/ha to about 96 g ai/ha and the compound of formula (I) or salt or ester thereof is applied at a rate from about 4 g acid equivalent per hectare (g ae/ha) to about 32 g ae/ha. In certain embodiments, the methods utilize the compound of formula (I), or its benzyl ester and carbaryl. In one embodiment, the methods utilize the compound of formula (I) and carbaryl, wherein the compound of formula (I) is applied at a rate of from about 4 g acid equivalent per hectare (g ae/ha) to about 32 g ae/ha, and carbaryl is applied at a rate of about 3 g ai/ha to about 96 g ai/ha. In one embodiment, the methods utilize the benzyl ester of the compound of formula (I) and carbaryl wherein the benzyl ester of the compound of formula (I) is applied at a rate of from about 4.4 g acid equivalent per hectare (g ae/ha) to about 32 g ae/ha, and carbaryl is applied at a rate of about 3 g ai/ha to about 96 g ai/ha.

In certain embodiments of the compositions and methods described herein, the compound of formula (I) or salt or ester thereof is used in combination with carbofuran. With respect to the compositions, in some embodiments, the weight ratio of the compound of formula (I) or salt or ester thereof to carbofuran is within the range of from about 1:1500 to about 30:1. In certain embodiments, the weight ratio of the compound of formula (I) or salt or ester thereof to carbofuran is within the range of from about 1:114 to about 1:4.

With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 52 grams active ingredient per hectare (g ai/ha) to about 3,300 g ai/ha based on the total amount of active ingredients in the composition. In certain embodiments, the composition is applied at an application rate of from about 79 grams active ingredient per hectare (g ai/ha) to about 520 g ai/ha based on the total amount of active ingredients in the composition.

In some embodiments, the methods comprise contacting the undesirable vegetation or locus thereof or applying to the soil or water to prevent the emergence or growth of vegetation with a compound of formula (I) or salt or ester thereof and carbofuran, e.g., sequentially or simultaneously. In some embodiments, carbofuran is applied at a rate from about 50 g ai/ha to about 3,000 g ai/ha and the compound of formula (I) or salt or ester thereof is applied at a rate from about 2 g ae/ha to about 300 g ae/ha. In some embodiments, carbofuran is applied at a rate from about 125 g ai/ha to about 500 g ai/ha and the compound of formula (I) or salt or ester thereof is applied at a rate from about 4 g acid equivalent per hectare (g ae/ha) to about 32 g ae/ha. In certain embodiments, the methods utilize the compound of formula (I), or its benzyl ester and carbofuran. In one embodiment, the methods utilize the compound of formula (I) and carbofuran, wherein the compound of formula (I) is applied at a rate of from about 2 g acid equivalent per hectare (g ae/ha) to about 300 g ae/ha, and carbaryl is applied at a rate of about 10 g ai/ha to about 3,000 g ai/ha. In one embodiment, the methods utilize the benzyl ester of the compound of formula (I) and carbofuran, wherein the benzyl ester of the compound of formula (I) is applied at a rate of from about 4.4 g acid equivalent per hectare (g ae/ha) to about 32 g ae/ha, and carbofuran is applied at a rate of about 125 g ai/ha to about 500 g ai/ha.

In certain embodiments of the compositions and methods described herein, the compound of formula (I) or salt or ester thereof is used in combination with cartap. With respect to the compositions, in some embodiments, the weight ratio of the compound of formula (I) or salt or ester thereof to cartap is within the range of from about 1:500 to about 1:1.5. In certain embodiments, the weight ratio of the compound of formula (I) or salt or ester thereof to cartap is within the range of from about 1:63 to about 1:8.

With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 402 grams active ingredient per hectare (g ai/ha) to about 1,300 g ai/ha based on the total amount of active ingredients in the composition. In certain embodiments, the composition is applied at an application rate of from about 258 grams active ingredient per hectare (g ai/ha) to about 532 g ai/ha based on the total amount of active ingredients in the composition.

In some embodiments, the methods comprise contacting the undesirable vegetation or locus thereof or applying to the soil or water to prevent the emergence or growth of vegetation with a compound of formula (I) or salt or ester thereof and cartap, e.g., sequentially or simultaneously. In some embodiments, cartap is applied at a rate from about 400 g ai/ha to about 1,000 g ai/ha and the compound of formula (I) or salt or ester thereof is applied at a rate from about 2 g ae/ha to about 300 g ae/ha. In some embodiments, cartap is applied at a rate from about 250 g ai/ha to about 500 g ai/ha and the compound of formula (I) or salt or ester thereof is applied at a rate from about 8 g acid equivalent per hectare (g ae/ha) to about 32 g ae/ha. In certain embodiments, the methods utilize the compound of formula (I), or its benzyl ester and cartap. In one embodiment, the methods utilize the compound of formula (I) and cartap, wherein the compound of formula (I) is applied at a rate of from about 8 g acid equivalent per hectare (g ae/ha) to about 32 g ae/ha, and cartap is applied at a rate of about 250 g ai/ha to about 500 g ai/ha. In one embodiment, the methods utilize the benzyl ester of the compound of formula (I) and cartap, wherein the benzyl ester of the compound of formula (I) is applied at a rate of from about 8 g acid equivalent per hectare (g ae/ha) to about 32 g ae/ha, and cartap is applied at a rate of about 250 g ai/ha to about 500 g ai/ha.

In certain embodiments of the compositions and methods described herein, the compound of formula (I) or salt or ester thereof is used in combination with chlorpyrifos. With respect to the compositions, in some embodiments, the weight ratio of the compound of formula (I) or salt or ester thereof to chlorpyrifos is within the range of from about 1:500 to about 15:1. In certain embodiments, the weight ratio of the compound of formula (I) or salt or ester thereof to chlorpyrifos is within the range of from about 1:164 to about 1:6.

With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 22 grams active ingredient per hectare (g ai/ha) to about 1,300 g ai/ha based on the total amount of active ingredients in the composition. In certain embodiments, the composition is applied at an application rate of from about 184 grams active ingredient per hectare (g ai/ha) to about 752 g ai/ha based on the total amount of active ingredients in the composition.

In some embodiments, the methods comprise contacting the undesirable vegetation or locus thereof or applying to the soil or water to prevent the emergence or growth of vegetation with a compound of formula (I) or salt or ester thereof and chlorpyrifos, e.g., sequentially or simultaneously. In some embodiments, chlorpyrifos is applied at a rate from about 20 g ai/ha to about 1,000 g ai/ha and the compound of formula (I) or salt or ester thereof is applied at a rate from about 2 g ae/ha to about 300 g ae/ha. In some embodiments, chlorpyrifos is applied at a rate from about 180 g ai/ha to about 720 g ai/ha and the compound of formula (I) or salt or ester thereof is applied at a rate from about 4 g acid equivalent per hectare (g ae/ha) to about 32 g ae/ha. In certain embodiments, the methods utilize the compound of formula (I), or its benzyl ester and chlorpyrifos. In one embodiment, the methods utilize the compound of formula (I) and chlorpyrifos, wherein the compound of formula (I) is applied at a rate of from about 4 g acid equivalent per hectare (g ae/ha) to about 32 g ae/ha, and chlorpyrifos is applied at a rate of about 180 g ai/ha to about 720 g ai/ha. In one embodiment, the methods utilize the benzyl ester of the compound of formula (I) and chlorpyrifos, wherein the benzyl ester of the compound of formula (I) is applied at a rate of from about 4 g acid equivalent per hectare (g ae/ha) to about 32 g ae/ha, and chlorpyrifos is applied at a rate of about 180 g ai/ha to about 720 g ai/ha.

In certain embodiments of the compositions and methods described herein, the compound of formula (I) or salt or ester thereof is used in combination with cypermethrin. With respect to the compositions, in some embodiments, the weight ratio of the compound of formula (I) or salt or ester thereof to cypermethrin is within the range of from about 1:250 to about 150:1. In certain embodiments, the weight ratio of the compound of formula (I) or salt or ester thereof to cypermethrin is within the range of from about 1:8 to about 5:1.

With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 4 grams active ingredient per hectare (g ai/ha) to about 800 g ai/ha based on the total amount of active ingredients in the composition. In certain embodiments, the composition is applied at an application rate of from about 15 grams active ingredient per hectare (g ai/ha) to about 100 g ai/ha based on the total amount of active ingredients in the composition.

In some embodiments, the methods comprise contacting the undesirable vegetation or locus thereof or applying to the soil or water to prevent the emergence or growth of vegetation with a compound of formula (I) or salt or ester thereof and cypermethrin, e.g., sequentially or simultaneously. In some embodiments, cypermethrin is applied at a rate from about 2 g ai/ha to about 500 g ai/ha and the compound of formula (I) or salt or ester thereof is applied at a rate from about 2 g ae/ha to about 300 g ae/ha. In some embodiments, cypermethrin is applied at a rate from about 7 g ai/ha to about 60 g ai/ha and the compound of formula (I) or salt or ester thereof is applied at a rate from about 8 g acid equivalent per hectare (g ae/ha) to about 32 g ae/ha. In certain embodiments, the methods utilize the compound of formula (I), or its benzyl ester and cypermethrin. In one embodiment, the methods utilize the compound of formula (I) and cypermethrin, wherein the compound of formula (I) is applied at a rate of from about 8 g acid equivalent per hectare (g ae/ha) to about 32 g ae/ha, and cypermethrin is applied at a rate of about 7 g ai/ha to about 60 g ai/ha. In one embodiment, the methods utilize the benzyl ester of the compound of formula (I) and cypermethrin, wherein the benzyl ester of the compound of formula (I) is applied at a rate of from about 8 g acid equivalent per hectare (g ae/ha) to about 32 g ae/ha, and cypermethrin is applied at a rate of about 7 g ai/ha to about 60 g ai/ha.

In certain embodiments of the compositions and methods described herein, the compound of formula (I) or salt or ester thereof is used in combination with dimethoate. With respect to the compositions, in some embodiments, the weight ratio of the compound of formula (I) or salt or ester thereof to dimethoate is within the range of from about 1:500 to about 30:1. In certain embodiments, the weight ratio of the compound of formula (I) or salt or ester thereof to dimethoate is within the range of from about 1:205 to about 1:110.

With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 12 grams active ingredient per hectare (g ai/ha) to about 1,300 g ai/ha based on the total amount of active ingredients in the composition. In certain embodiments, the composition is applied at an application rate of from about 30 grams active ingredient per hectare (g ai/ha) to about 904 g ai/ha based on the total amount of active ingredients in the composition.

In some embodiments, the methods comprise contacting the undesirable vegetation or locus thereof or applying to the soil or water to prevent the emergence or growth of vegetation with a compound of formula (I) or salt or ester thereof and dimethoate, e.g., sequentially or simultaneously. In some embodiments, dimethoate is applied at a rate from about 10 g ai/ha to about 1,000 g ai/ha and the compound of formula (I) or salt or ester thereof is applied at a rate from about 2 g ae/ha to about 300 g ae/ha. In some embodiments, dimethoate is applied at a rate from about 25 g ai/ha to about 900 g ai/ha and the compound of formula (I) or salt or ester thereof is applied at a rate from about 4 g acid equivalent per hectare (g ae/ha) to about 5 g ae/ha. In certain embodiments, the methods utilize the compound of formula (I), or its benzyl ester and dimethoate. In one embodiment, the methods utilize the compound of formula (I) and dimethoate, wherein the compound of formula (I) is applied at a rate of from about 4.0 g acid equivalent per hectare (g ae/ha) to about 40 g ae/ha, and dimethoate is applied at a rate of about 25 g ai/ha to about 900 g ai/ha. In one embodiment, the methods utilize the benzyl ester of the compound of formula (I) and dimethoate, wherein the benzyl ester of the compound of formula (I) is applied at a rate of from about 4.0 g acid equivalent per hectare (g ae/ha) to about 40 g ae/ha, and dimethoate is applied at a rate of about 25 g ai/ha to about 900 g ai/ha.

In certain embodiments of the compositions and methods described herein, the compound of formula (I) or salt or ester thereof is used in combination with dinotefuran. With respect to the compositions, in some embodiments, the weight ratio of the compound of formula (I) or salt or ester thereof to dinotefuran is within the range of from about 1:500 to about 30:1. In certain embodiments, the weight ratio of the compound of formula (I) or salt or ester thereof to dinotefuran is within the range of from about 1:450 to about 10:1.

With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 12 grams active ingredient per hectare (g ai/ha) to about 1,300 g ai/ha based on the total amount of active ingredients in the composition. In certain embodiments, the composition is applied at an application rate of from about 22 grams active ingredient per hectare (g ai/ha) to about 1,100 g ai/ha based on the total amount of active ingredients in the composition.

In some embodiments, the methods comprise contacting the undesirable vegetation or locus thereof or applying to the soil or water to prevent the emergence or growth of vegetation with a compound of formula (I) or salt or ester thereof and dinotefuran, e.g., sequentially or simultaneously. In some embodiments, dinotefuran is applied at a rate from about 10 g ai/ha to about 1,000 g ai/ha and the compound of formula (I) or salt or ester thereof is applied at a rate from about 2 g ae/ha to about 300 g ae/ha. In some embodiments, dinotefuran is applied at a rate from about 20 g ai/ha to about 900 g ai/ha and the compound of formula (I) or salt or ester thereof is applied at a rate from about 2 g acid equivalent per hectare (g ae/ha) to about 200 g ae/ha. In certain embodiments, the methods utilize the compound of formula (I), or its benzyl ester and dinotefuran. In one embodiment, the methods utilize the compound of formula (I) and dinotefuran, wherein the compound of formula (I) is applied at a rate of from about 2 g acid equivalent per hectare (g ae/ha) to about 200 g ae/ha, and dinotefuran is applied at a rate of about 20 g ai/ha to about 900 g ai/ha. In one embodiment, the methods utilize the benzyl ester of the compound of formula (I) and dinotefuran, wherein the benzyl ester of the compound of formula (I) is applied at a rate of from about 2 g acid equivalent per hectare (g ae/ha) to about 200 g ae/ha, and dinotefuran is applied at a rate of about 20 g ai/ha to about 900 g ai/ha.

In certain embodiments of the compositions and methods described herein, the compound of formula (I) or salt or ester thereof is used in combination with etofenprox. With respect to the compositions, in some embodiments, the weight ratio of the compound of formula (I) or salt or ester thereof to etofenprox is within the range of from about 1:500 to about 30:1. In certain embodiments, the weight ratio of the compound of formula (I) or salt or ester thereof to etofenprox is within the range of from about 1:75 to about 1:2.

With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 12 grams active ingredient per hectare (g ai/ha) to about 1,300 g ai/ha based on the total amount of active ingredients in the composition. In certain embodiments, the composition is applied at an application rate of from about 83 grams active ingredient per hectare (g ai/ha) to about 332 g ai/ha based on the total amount of active ingredients in the composition.

In some embodiments, the methods comprise contacting the undesirable vegetation or locus thereof or applying to the soil or water to prevent the emergence or growth of vegetation with a compound of formula (I) or salt or ester thereof and etofenprox, e.g., sequentially or simultaneously. In some embodiments, etofenprox is applied at a rate from about 10 g ai/ha to about 1,000 g ai/ha and the compound of formula (I) or salt or ester thereof is applied at a rate from about 2 g ae/ha to about 300 g ae/ha. In some embodiments, etofenprox is applied at a rate from about 75 g ai/ha to about 300 g ai/ha and the compound of formula (I) or salt or ester thereof is applied at a rate from about 8 g acid equivalent per hectare (g ae/ha) to about 32 g ae/ha. In certain embodiments, the methods utilize the compound of formula (I), or its benzyl ester and etofenprox. In one embodiment, the methods utilize the compound of formula (I) and etofenprox, wherein the compound of formula (I) is applied at a rate of from about 8 g acid equivalent per hectare (g ae/ha) to about 32 g ae/ha, and etofenprox is applied at a rate of about 75 g ai/ha to about 300 g ai/ha. In one embodiment, the methods utilize the benzyl ester of the compound of formula (I) and etofenprox, wherein the benzyl ester of the compound of formula (I) is applied at a rate of from about 8 g acid equivalent per hectare (g ae/ha) to about 32 g ae/ha, and etofenprox is applied at a rate of about 75 g ai/ha to about 300 g ai/ha.

In certain embodiments of the compositions and methods described herein, the compound of formula (I) or salt or ester thereof is used in combination with fenitrothion. With respect to the compositions, in some embodiments, the weight ratio of the compound of formula (I) or salt or ester thereof to fenitrothion is within the range of from about 1:500 to about 30:1. In certain embodiments, the weight ratio of the compound of formula (I) or salt or ester thereof to fenitrothion is within the range of from about 1:225 to about 8:1.

With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 12 grams active ingredient per hectare (g ai/ha) to about 1,300 g ai/ha based on the total amount of active ingredients in the composition. In certain embodiments, the composition is applied at an application rate of from about 29 grams active ingredient per hectare (g ai/ha) to about 1,100 g ai/ha based on the total amount of active ingredients in the composition.

In some embodiments, the methods comprise contacting the undesirable vegetation or locus thereof or applying to the soil or water to prevent the emergence or growth of vegetation with a compound of formula (I) or salt or ester thereof and fenitrothion, e.g., sequentially or simultaneously. In some embodiments, fenitrothionis applied at a rate from about 10 g ai/ha to about 1,000 g ai/ha and the compound of formula (I) or salt or ester thereof is applied at a rate from about 2 g ae/ha to about 300 g ae/ha. In some embodiments, fenitrothion is applied at a rate from about 25 g ai/ha to about 900 g ai/ha and the compound of formula (I) or salt or ester thereof is applied at a rate from about 4 g acid equivalent per hectare (g ae/ha) to about 200 g ae/ha. In certain embodiments, the methods utilize the compound of formula (I), or its benzyl ester and fenitrothion. In one embodiment, the methods utilize the compound of formula (I) and fenitrothion, wherein the compound of formula (I) is applied at a rate of from about 4 g acid equivalent per hectare (g ae/ha) to about 200 g ae/ha, and fenitrothion is applied at a rate of about 25 g ai/ha to about 900 g ai/ha. In one embodiment, the methods utilize the benzyl ester of the compound of formula (I) and fenitrothion, wherein the benzyl ester of the compound of formula (I) is applied at a rate of from about 4 g acid equivalent per hectare (g ae/ha) to about 200 g ae/ha, and fenitrothion is applied at a rate of about 25 g ai/ha to about 900 g ai/ha.

In certain embodiments of the compositions and methods described herein, the compound of formula (I) or salt or ester thereof is used in combination with fipronil. With respect to the compositions, in some embodiments, the weight ratio of the compound of formula (I) or salt or ester thereof to fipronil is within the range of from about 1:500 to about 300:1. In certain embodiments, the weight ratio of the compound of formula (I) or salt or ester thereof to fipronil is within the range of from about 1:205 to about 5:1.

With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 3 grams active ingredient per hectare (g ai/ha) to about 1,300 g ai/ha based on the total amount of active ingredients in the composition. In certain embodiments, the composition is applied at an application rate of from about 7 grams active ingredient per hectare (g ai/ha) to about 940 g ai/ha based on the total amount of active ingredients in the composition.

In some embodiments, the methods comprise contacting the undesirable vegetation or locus thereof or applying to the soil or water to prevent the emergence or growth of vegetation with a compound of formula (I) or salt or ester thereof and fipronil, e.g., sequentially or simultaneously. In some embodiments, fipronil is applied at a rate from about 1 g ai/ha to about 1,000 g ai/ha and the compound of formula (I) or salt or ester thereof is applied at a rate from about 2 g ae/ha to about 300 g ae/ha. In some embodiments, fipronil is applied at a rate from about 3 g ai/ha to about 900 g ai/ha and the compound of formula (I) or salt or ester thereof is applied at a rate from about 4 g acid equivalent per hectare (g ae/ha) to about 40 g ae/ha. In certain embodiments, the methods utilize the compound of formula (I), or its benzyl ester and fipronil. In one embodiment, the methods utilize the compound of formula (I) and fipronil, wherein the compound of formula (I) is applied at a rate of from about 4 g acid equivalent per hectare (g ae/ha) to about 40 g ae/ha, and fipronil is applied at a rate of about 3 g ai/ha to about 900 g ai/ha. In one embodiment, the methods utilize the benzyl ester of the compound of formula (I) and fipronil, wherein the benzyl ester of the compound of formula (I) is applied at a rate of from about 4 g acid equivalent per hectare (g ae/ha) to about 40 g ae/ha, and fipronil is applied at a rate of about 3 g ai/ha to about 900 g ai/ha.

In certain embodiments of the compositions and methods described herein, the compound of formula (I) or salt or ester thereof is used in combination with imidacloprid. With respect to the compositions, in some embodiments, the weight ratio of the compound of formula (I) or salt or ester thereof to imidacloprid is within the range of from about 1:500 to about 60:1. In certain embodiments, the weight ratio of the compound of formula (I) or salt or ester thereof to imidacloprid is within the range of from about 1:205 to about 1:1.

With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 7 grams active ingredient per hectare (g ai/ha) to about 1,300 g ai/ha based on the total amount of active ingredients in the composition. In certain embodiments, the composition is applied at an application rate of from about 29 grams active ingredient per hectare (g ai/ha) to about 940 g ai/ha based on the total amount of active ingredients in the composition.

In some embodiments, the methods comprise contacting the undesirable vegetation or locus thereof or applying to the soil or water to prevent the emergence or growth of vegetation with a compound of formula (I) or salt or ester thereof and imidacloprid, e.g., sequentially or simultaneously. In some embodiments, imidacloprid is applied at a rate from about 5 g ai/ha to about 1,000 g ai/ha and the compound of formula (I) or salt or ester thereof is applied at a rate from about 2 g ae/ha to about 300 g ae/ha. In some embodiments, imidacloprid is applied at a rate from about 20 g ai/ha to about 900 g ai/ha and the compound of formula (I) or salt or ester thereof is applied at a rate from about 4 g acid equivalent per hectare (g ae/ha) to about 40 g ae/ha. In certain embodiments, the methods utilize the compound of formula (I), or its benzyl ester and imidacloprid. In one embodiment, the methods utilize the compound of formula (I) and imidacloprid, wherein the compound of formula (I) is applied at a rate of from about 4 g acid equivalent per hectare (g ae/ha) to about 40 g ae/ha, and imidacloprid is applied at a rate of about 25 g ai/ha to about 900 g ai/ha. In one embodiment, the methods utilize the benzyl ester of the compound of formula (I) and imidacloprid, wherein the benzyl ester of the compound of formula (I) is applied at a rate of from about 4 g acid equivalent per hectare (g ae/ha) to about 40 g ae/ha, and imidacloprid is applied at a rate of about 25 g ai/ha to about 900 g ai/ha.

In certain embodiments of the compositions and methods described herein, the compound of formula (I) or salt or ester thereof is used in combination with lambda-cyhalothrin. With respect to the compositions, in some embodiments, the weight ratio of the compound of formula (I) or salt or ester thereof to lambda-cyhalothrin is within the range of from about 1:500 to about 60:1. In certain embodiments, the weight ratio of the compound of formula (I) or salt or ester thereof to lambda-cyhalothrin is within the range of from about 1:205 to about 2:1.

With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 7 grams active ingredient per hectare (g ai/ha) to about 1,300 g ai/ha based on the total amount of active ingredients in the composition. In certain embodiments, the composition is applied at an application rate of from about 14 grams active ingredient per hectare (g ai/ha) to about 940 g ai/ha based on the total amount of active ingredients in the composition.

In some embodiments, the methods comprise contacting the undesirable vegetation or locus thereof or applying to the soil or water to prevent the emergence or growth of vegetation with a compound of formula (I) or salt or ester thereof and lambda-cyhalothrin, e.g., sequentially or simultaneously. In some embodiments, lambda-cyhalothrin is applied at a rate from about 5 g ai/ha to about 1,000 g ai/ha and the compound of formula (I) or salt or ester thereof is applied at a rate from about 2 g ae/ha to about 300 g ae/ha. In some embodiments, lambda-cyhalothrin is applied at a rate from about 10 g ai/ha to about 900 g ai/ha and the compound of formula (I) or salt or ester thereof is applied at a rate from about 4 g acid equivalent per hectare (g ae/ha) to about 40 g ae/ha. In certain embodiments, the methods utilize the compound of formula (I), or its benzyl ester and lambda-cyhalothrin. In one embodiment, the methods utilize the compound of formula (I) and lambda-cyhalothrin, wherein the compound of formula (I) is applied at a rate of from about 4 g acid equivalent per hectare (g ae/ha) to about 40 g ae/ha, and lambda-cyhalothrin is applied at a rate of about 10 g ai/ha to about 900 g ai/ha. In one embodiment, the methods utilize the benzyl ester of the compound of formula (I) and lambda-cyhalothrin wherein the benzyl ester of the compound of formula (I) is applied at a rate of from about 4 g acid equivalent per hectare (g ae/ha) to about 40 g ae/ha, and lambda-cyhalothrin is applied at a rate of about 10 g ai/ha to about 900 g ai/ha.

In certain embodiments of the compositions and methods described herein, the compound of formula (I) or salt or ester thereof is used in combination with malathion. With respect to the compositions, in some embodiments, the weight ratio of the compound of formula (I) or salt or ester thereof to malathion is within the range of from about 1:500 to about 150:1. In certain embodiments, the weight ratio of the compound of formula (I) or salt or ester thereof to malathion is within the range of from about 1:70 to about 1:5.

With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 4 grams active ingredient per hectare (g ai/ha) to about 1,300 g ai/ha based on the total amount of active ingredients in the composition. In certain embodiments, the composition is applied at an application rate of from about 148 grams active ingredient per hectare (g ai/ha) to about 592 g ai/ha based on the total amount of active ingredients in the composition.

In some embodiments, the methods comprise contacting the undesirable vegetation or locus thereof or applying to the soil or water to prevent the emergence or growth of vegetation with a compound of formula (I) or salt or ester thereof and malathion, e.g., sequentially or simultaneously. In some embodiments, malathion is applied at a rate from about 2 g ai/ha to about 1,000 g ai/ha and the compound of formula (I) or salt or ester thereof is applied at a rate from about 2 g ae/ha to about 300 g ae/ha. In some embodiments, malathion is applied at a rate from about 140 g ai/ha to about 560 g ai/ha and the compound of formula (I) or salt or ester thereof is applied at a rate from about 8 g acid equivalent per hectare (g ae/ha) to about 32 g ae/ha. In certain embodiments, the methods utilize the compound of formula (I), or its benzyl ester and malathion. In one embodiment, the methods utilize the compound of formula (I) and malathion, wherein the compound of formula (I) is applied at a rate of from about 8 g acid equivalent per hectare (g ae/ha) to about 32 g ae/ha, and malathion is applied at a rate of about 140 g ai/ha to about 560 g ai/ha. In one embodiment, the methods utilize the benzyl ester of the compound of formula (I) and malathion, wherein the benzyl ester of the compound of formula (I) is applied at a rate of from about 8 g acid equivalent per hectare (g ae/ha) to about 32 g ae/ha, and malathion is applied at a rate of about 140 g ai/ha to about 560 g ai/ha.

In certain embodiments of the compositions and methods described herein, the compound of formula (I) or salt or ester thereof is used in combination with methamidophos. With respect to the compositions, in some embodiments, the weight ratio of the compound of formula (I) or salt or ester thereof to methamidophos is within the range of from about 1:1000 to about 30:1. In certain embodiments, the weight ratio of the compound of formula (I) or salt or ester thereof to methamidophos is within the range of from about 1:28 to about 1:4.

With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 12 grams active ingredient per hectare (g ai/ha) to about 2,300 g ai/ha based on the total amount of active ingredients in the composition. In certain embodiments, the composition is applied at an application rate of from about 120 grams active ingredient per hectare (g ai/ha) to about 256 g ai/ha based on the total amount of active ingredients in the composition.

In some embodiments, the methods comprise contacting the undesirable vegetation or locus thereof or applying to the soil or water to prevent the emergence or growth of vegetation with a compound of formula (I) or salt or ester thereof and methamidophos, e.g., sequentially or simultaneously. In some embodiments, methamidophos is applied at a rate from about 10 g ai/ha to about 2,000 g ai/ha and the compound of formula (I) or salt or ester thereof is applied at a rate from about 2 g ae/ha to about 300 g ae/ha. In some embodiments, methamidophos is applied at a rate from about 112 g ai/ha to about 224 g ai/ha and the compound of formula (I) or salt or ester thereof is applied at a rate from about 8 g acid equivalent per hectare (g ae/ha) to about 32 g ae/ha. In certain embodiments, the methods utilize the compound of formula (I), or its benzyl ester and methamidophos. In one embodiment, the methods utilize the compound of formula (I) and methamidophos, wherein the compound of formula (I) is applied at a rate of from about 8 g acid equivalent per hectare (g ae/ha) to about 32 g ae/ha, and methamidophos is applied at a rate of about 112 g ai/ha to about 224 g ai/ha. In one embodiment, the methods utilize the benzyl ester of the compound of formula (I) and methamidophos wherein the benzyl ester of the compound of formula (I) is applied at a rate of from about 8 g acid equivalent per hectare (g ae/ha) to about 32 g ae/ha, and methamidophos is applied at a rate of about 112 g ai/ha to about 224 g ai/ha.

In certain embodiments of the compositions and methods described herein, the compound of formula (I) or salt or ester thereof is used in combination with piperonyl butoxide. With respect to the compositions, in some embodiments, the weight ratio of the compound of formula (I) or salt or ester thereof to piperonyl butoxide is within the range of from about 1:1500 to about 150:1. In certain embodiments, the weight ratio of the compound of formula (I) or salt or ester thereof to piperonyl butoxide is within the range of from about 1:70 to about 1:5.

With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 4 grams active ingredient per hectare (g ai/ha) to about 3,300 g ai/ha based on the total amount of active ingredients in the composition. In certain embodiments, the composition is applied at an application rate of from about 148 grams active ingredient per hectare (g ai/ha) to about 592 g ai/ha based on the total amount of active ingredients in the composition.

In some embodiments, the methods comprise contacting the undesirable vegetation or locus thereof or applying to the soil or water to prevent the emergence or growth of vegetation with a compound of formula (I) or salt or ester thereof and piperonyl butoxide, e.g., sequentially or simultaneously. In some embodiments, piperonyl butoxide is applied at a rate from about 2 g ai/ha to about 3,000 g ai/ha and the compound of formula (I) or salt or ester thereof is applied at a rate from about 2 g ae/ha to about 300 g ae/ha. In some embodiments, piperonyl butoxide is applied at a rate from about 140 g ai/ha to about 560 g ai/ha and the compound of formula (I) or salt or ester thereof is applied at a rate from about 8 g acid equivalent per hectare (g ae/ha) to about 32 g ae/ha. In certain embodiments, the methods utilize the compound of formula (I), or its benzyl ester and piperonyl butoxide. In one embodiment, the methods utilize the compound of formula (I) and piperonyl butoxide, wherein the compound of formula (I) is applied at a rate of from about 8 g acid equivalent per hectare (g ae/ha) to about 3 g ae/ha, and piperonyl butoxide is applied at a rate of about 140 g ai/ha to about 560 g ai/ha. In one embodiment, the methods utilize the benzyl ester of the compound of formula (I) and piperonyl butoxide, wherein the benzyl ester of the compound of formula (I) is applied at a rate of from about 8 g acid equivalent per hectare (g ae/ha) to about 32 g ae/ha, and piperonyl butoxide is applied at a rate of about 140 g ai/ha to about 560 g ai/ha.

In certain embodiments of the compositions and methods described herein, the compound of formula (I) or salt or ester thereof is used in combination with pymetrozine. With respect to the compositions, in some embodiments, the weight ratio of the compound of formula (I) or salt or ester thereof to pymetrozine is within the range of from about 1:500 to about 60:1. In certain embodiments, the weight ratio of the compound of formula (I) or salt or ester thereof to pymetrozine is within the range of from about 1:450 to about 20:1.

With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 7 grams active ingredient per hectare (g ai/ha) to about 1,300 g ai/ha based on the total amount of active ingredients in the composition. In certain embodiments, the composition is applied at an application rate of from about 12 grams active ingredient per hectare (g ai/ha) to about 1,100 g ai/ha based on the total amount of active ingredients in the composition.

In some embodiments, the methods comprise contacting the undesirable vegetation or locus thereof or applying to the soil or water to prevent the emergence or growth of vegetation with a compound of formula (I) or salt or ester thereof and pymetrozine, e.g., sequentially or simultaneously. In some embodiments, pymetrozine is applied at a rate from about 5 g ai/ha to about 1,000 g ai/ha and the compound of formula (I) or salt or ester thereof is applied at a rate from about 2 g ae/ha to about 300 g ae/ha. In some embodiments, pymetrozine is applied at a rate from about 10 g ai/ha to about 900 g ai/ha and the compound of formula (I) or salt or ester thereof is applied at a rate from about 10 g acid equivalent per hectare (g ae/ha) to about 140 g ae/ha. In certain embodiments, the methods utilize the compound of formula (I), or its benzyl ester and pymetrozine. In one embodiment, the methods utilize the compound of formula (I) and pymetrozine, wherein the compound of formula (I) is applied at a rate of from about 2 g acid equivalent per hectare (g ae/ha) to about 140 g ae/ha, and pymetrozine is applied at a rate of about 10 g ai/ha to about 900 g ai/ha. In one embodiment, the methods utilize the benzyl ester of the compound of formula (I) and pymetrozine, wherein the benzyl ester of the compound of formula (I) is applied at a rate of from about 2 g acid equivalent per hectare (g ae/ha) to about 140 g ae/ha, and pymetrozine is applied at a rate of about 10 g ai/ha to about 900 g ai/ha.

In certain embodiments of the compositions and methods described herein, the compound of formula (I) or salt or ester thereof is used in combination with spinetoram. With respect to the compositions, in some embodiments, the weight ratio of the compound of formula (I) or salt or ester thereof to spinetoram is within the range of from about 1:500 to about 150:1. In certain embodiments, the weight ratio of the compound of formula (I) or salt or ester thereof to spinetoram is within the range of from about 1:15 to about 1:1.

With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 4 grams active ingredient per hectare (g ai/ha) to about 1,300 g ai/ha based on the total amount of active ingredients in the composition. In certain embodiments, the composition is applied at an application rate of from about 38 grams active ingredient per hectare (g ai/ha) to about 152 g ai/ha based on the total amount of active ingredients in the composition.

In some embodiments, the methods comprise contacting the undesirable vegetation or locus thereof or applying to the soil or water to prevent the emergence or growth of vegetation with a compound of formula (I) or salt or ester thereof and spinetoram, e.g., sequentially or simultaneously. In some embodiments, spinetoram is applied at a rate from about 2 g ai/ha to about 1,000 g ai/ha and the compound of formula (I) or salt or ester thereof is applied at a rate from about 2 g ae/ha to about 300 g ae/ha. In some embodiments, spinetoram is applied at a rate from about 30 g ai/ha to about 120 g ai/ha and the compound of formula (I) or salt or ester thereof is applied at a rate from about 8 g acid equivalent per hectare (g ae/ha) to about 32 g ae/ha. In certain embodiments, the methods utilize the compound of formula (I), or its benzyl ester and spinetoram. In one embodiment, the methods utilize the compound of formula (I) and spinetoram, wherein the compound of formula (I) is applied at a rate of from about 8 g acid equivalent per hectare (g ae/ha) to about 32 g ae/ha, and spinetoram is applied at a rate of about 30 g ai/ha to about 120 g ai/ha. In one embodiment, the methods utilize the benzyl ester of the compound of formula (I) and spinetoram, wherein the benzyl ester of the compound of formula (I) is applied at a rate of from about 8 g acid equivalent per hectare (g ae/ha) to about 32 g ae/ha, and spinetoram is applied at a rate of about 30 g ai/ha to about 120 g ai/ha.

In certain embodiments of the compositions and methods described herein, the compound of formula (I) or salt or ester thereof is used in combination with spinosad. With respect to the compositions, in some embodiments, the weight ratio of the compound of formula (I) or salt or ester thereof to spinosad is within the range of from about 1:500 to about 150:1. In certain embodiments, the weight ratio of the compound of formula (I) or salt or ester thereof to spinosad is within the range of from about 1:30 to about 1:1.

With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 4 grams active ingredient per hectare (g ai/ha) to about 1,300 g ai/ha based on the total amount of active ingredients in the composition. In certain embodiments, the composition is applied at an application rate of from about 78 grams active ingredient per hectare (g ai/ha) to about 312 g ai/ha based on the total amount of active ingredients in the composition.

In some embodiments, the methods comprise contacting the undesirable vegetation or locus thereof or applying to the soil or water to prevent the emergence or growth of vegetation with a compound of formula (I) or salt or ester thereof and spinosad, e.g., sequentially or simultaneously. In some embodiments, spinosad is applied at a rate from about 2 g ai/ha to about 1,000 g ai/ha and the compound of formula (I) or salt or ester thereof is applied at a rate from about 2 g ae/ha to about 300 g ae/ha. In some embodiments, spinosad is applied at a rate from about 70 g ai/ha to about 280 g ai/ha and the compound of formula (I) or salt or ester thereof is applied at a rate from about 8 g acid equivalent per hectare (g ae/ha) to about 32 g ae/ha. In certain embodiments, the methods utilize the compound of formula (I), or its benzyl ester and spinosad. In one embodiment, the methods utilize the compound of formula (I) and spinosad, wherein the compound of formula (I) is applied at a rate of from about 8 g acid equivalent per hectare (g ae/ha) to about 32 g ae/ha, and spinosad is applied at a rate of about 70 g ai/ha to about 280 g ai/ha. In one embodiment, the methods utilize the benzyl ester of the compound of formula (I) and spinosad, wherein the benzyl ester of the compound of formula (I) is applied at a rate of from about 8 g acid equivalent per hectare (g ae/ha) to about 32 g ae/ha, and spinosad is applied at a rate of about 70 g ai/ha to about 280 g ai/ha.

In certain embodiments of the compositions and methods described herein, the compound of formula (I) or salt or ester thereof is used in combination with sulfoxaflor. With respect to the compositions, in some embodiments, the weight ratio of the compound of formula (I) or salt or ester thereof to sulfoxaflor is within the range of from about 1:500 to about 150:1. In certain embodiments, the weight ratio of the compound of formula (I) or salt or ester thereof to sulfoxaflor is within the range of from about 1:34 to about 3:1.

With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 4 grams active ingredient per hectare (g ai/ha) to about 1,300 g ai/ha based on the total amount of active ingredients in the composition. In certain embodiments, the composition is applied at an application rate of from about 17 grams active ingredient per hectare (g ai/ha) to about 184 g ai/ha based on the total amount of active ingredients in the composition.

In some embodiments, the methods comprise contacting the undesirable vegetation or locus thereof or applying to the soil or water to prevent the emergence or growth of vegetation with a compound of formula (I) or salt or ester thereof and sulfoxaflor, e.g., sequentially or simultaneously. In some embodiments, sulfoxafloris applied at a rate from about 2 g ai/ha to about 1,000 g ai/ha and the compound of formula (I) or salt or ester thereof is applied at a rate from about 2 g ae/ha to about 300 g ae/ha. In some embodiments, sulfoxaflor is applied at a rate from about 12.5 g ai/ha to about 150 g ai/ha and the compound of formula (I) or salt or ester thereof is applied at a rate from about 4 g acid equivalent per hectare (g ae/ha) to about 32 g ae/ha. In certain embodiments, the methods utilize the compound of formula (I), or its benzyl ester and sulfoxaflor. In one embodiment, the methods utilize the compound of formula (I) and sulfoxaflor, wherein the compound of formula (I) is applied at a rate of from about 4 g acid equivalent per hectare (g ae/ha) to about 32 g ae/ha, and sulfoxaflor is applied at a rate of about 12.5 g ai/ha to about 150 g ai/ha. In one embodiment, the methods utilize the benzyl ester of the compound of formula (I) and sulfoxaflor, wherein the benzyl ester of the compound of formula (I) is applied at a rate of from about 4 g acid equivalent per hectare (g ae/ha) to about 32 g ae/ha, and sulfoxaflor is applied at a rate of about 12.5 g ai/ha to about 150 g ai/ha.

In certain embodiments of the compositions and methods described herein, the compound of formula (I) or salt or ester thereof is used in combination with triazophos. With respect to the compositions, in some embodiments, the weight ratio of the compound of formula (I) or salt or ester thereof to triazophos is within the range of from about 1:500 to about 30:1. In certain embodiments, the weight ratio of the compound of formula (I) or salt or ester thereof to triazophos is within the range of from about 1:47 to about 1:3.

With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 12 grams active ingredient per hectare (g ai/ha) to about 1,300 g ai/ha based on the total amount of active ingredients in the composition. In certain embodiments, the composition is applied at an application rate of from about 108 grams active ingredient per hectare (g ai/ha) to about 407 g ai/ha based on the total amount of active ingredients in the composition.

In some embodiments, the methods comprise contacting the undesirable vegetation or locus thereof or applying to the soil or water to prevent the emergence or growth of vegetation with a compound of formula (I) or salt or ester thereof and triazophos, e.g., sequentially or simultaneously. In some embodiments, triazophos is applied at a rate from about 10 g ai/ha to about 1,000 g ai/ha and the compound of formula (I) or salt or ester thereof is applied at a rate from about 2 g ae/ha to about 300 g ae/ha. In some embodiments, triazophos is applied at a rate from about 100 g ai/ha to about 375 g ai/ha and the compound of formula (I) or salt or ester thereof is applied at a rate from about 8 g acid equivalent per hectare (g ae/ha) to about 32 g ae/ha. In certain embodiments, the methods utilize the compound of formula (I), or its benzyl ester and triazophos. In one embodiment, the methods utilize the compound of formula (I) and triazophos, wherein the compound of formula (I) is applied at a rate of from about 8 g acid equivalent per hectare (g ae/ha) to about 32 g ae/ha, and triazophos is applied at a rate of about 100 g ai/ha to about 375 g ai/ha. In one embodiment, the methods utilize the benzyl ester of the compound of formula (I) and triazophos, wherein the benzyl ester of the compound of formula (I) is applied at a rate of from about 8 g acid equivalent per hectare (g ae/ha) to about 32 g ae/ha, and triazophosis applied at a rate of about 100 g ai/ha to about 375 g ai/ha.

In certain embodiments, the methods and compositions utilizing the compound of formula (I) or salt or ester thereof in combination with acephate, carbaryl, carbofuran, cartap, chlorpyrifos, cypermethrin, dimethoate, dinotefuran, etofenprox, fenitrothion, fipronil, imidacloprid, lambda-cyhalothrin, malathion, methamidophos, piperonyl butoxide, pymetrozine, spinetoram, spinosad, sulfoxaflor and triazophos are used to control BRAPP, CYPES, CYPIR, CYPRO, DIGSA, ECHCG, ECHCO, IPOHE, LEFCH, LEFFA, LEFPA, SCPMA AND SCPJU.

The components of the mixtures described herein can be applied either separately or as part of a multipart herbicidal system.

The mixtures described herein can be applied in conjunction with one or more other herbicides to control a wider variety of undesirable vegetation. When used in conjunction with other herbicides, the composition can be formulated with the other herbicide or herbicides, tank mixed with the other herbicide or herbicides or applied sequentially with the other herbicide or herbicides. Some of the herbicides that can be employed in conjunction with the compositions and methods described herein include, but are not limited to: 4-CPA, 4-CPB, 4-CPP, 2,4-D, 2,4-D choline salt, 2,4-D esters and amines, 2,4-DB, 3,4-DA, 3,4-DB, 2,4-DEB, 2,4-DEP, 3,4-DP, 2,3,6-TBA, 2,4,5-T, 2,4,5-TB, acetochlor, acifluorfen, aclonifen, acrolein, alachlor, allidochlor, alloxydim, allyl alcohol, alorac, ametridione, ametryn, amibuzin, amicarbazone, amidosulfuron, aminocyclopyrachlor, aminopyralid, amiprofos-methyl, amitrole, ammonium sulfamate, anilofos, anisuron, asulam, atraton, atrazine, azafenidin, azimsulfuron, aziprotryne, barban, BCPC, beflubutamid, benazolin, bencarbazone, benfluralin, benfuresate, bensulfuron-methyl, bensulide, benthiocarb, bentazon-sodium, benzadox, benzfendizone, benzipram, benzobicyclon, benzofenap, benzofluor, benzoylprop, benzthiazuron, bialaphos, bicyclopyrone, bifenox, bilanafos, bispyribac-sodium, borax, bromacil, bromobonil, bromobutide, bromofenoxim, bromoxynil, brompyrazon, butachlor, butafenacil, butamifos, butenachlor, buthidazole, buthiuron, butralin, butroxydim, buturon, butylate, cacodylic acid, cafenstrole, calcium chlorate, calcium cyanamide, cambendichlor, carbasulam, carbetamide, carboxazole, chlorprocarb, carfentrazone-ethyl, CDEA, CEPC, chlomethoxyfen, chloramben, chloranocryl, chlorazifop, chlorazine, chlorbromuron, chlorbufam, chloreturon, chlorfenac, chlorfenprop, chlorflurazole, chlorflurenol, chloridazon, chlorimuron, chlornitrofen, chloropon, chlorotoluron, chloroxuron, chloroxynil, chlorpropham, chlorsulfuron, chlorthal, chlorthiamid, cinidon-ethyl, cinmethylin, cinosulfuron, cisanilide, clethodim, cliodinate, clodinafop-propargyl, clofop, clomeprop, cloprop, cloproxydim, clopyralid, cloransulam-methyl, CMA, copper sulfate, CPMF, CPPC, credazine, cresol, cumyluron, cyanatryn, cyanazine, cycloate, cyclopyrimorate, cyclosulfamuron, cycloxydim, cycluron, cyhalofop-butyl, cyperquat, cyprazine, cyprazole, cypromid, daimuron, dalapon, dazomet, delachlor, desmedipham, desmetryn, di-allate, dicamba, dichlobenil, dichloralurea, dichlormate, dichlorprop, dichlorprop-P, diclofop-methyl, diclosulam, diethamquat, diethatyl, difenopenten, difenoxuron, difenzoquat, diflufenican, diflufenzopyr, dimefuron, dimepiperate, dimethachlor, dimethametryn, dimethenamid, dimethenamid-P, dimexano, dimidazon, dinitramine, dinofenate, dinoprop, dinosam, dinoseb, dinoterb, diphenamid, dipropetryn, diquat, disul, dithiopyr, diuron, DMPA, DNOC, DSMA, EBEP, eglinazine, endothal, epronaz, EPTC, erbon, esprocarb, ethalfluralin, ethbenzamide, ethametsulfuron, ethidimuron, ethiolate, ethobenzamid, etobenzamid, ethofumesate, ethoxyfen, ethoxysulfuron, etinofen, etnipromid, etobenzanid, EXD, fenasulam, fenoprop, fenoxaprop, fenoxaprop-P-ethyl, fenoxaprop-P-ethyl+isoxadifen-ethyl, fenoxasulfone, fenteracol, fenthiaprop, fentrazamide, fenuron, ferrous sulfate, flamprop, flamprop-M, flazasulfuron, florasulam, fluazifop, fluazifop-P-butyl, fluazolate, flucarbazone, flucetosulfuron, fluchloralin, flufenacet, flufenican, flufenpyr-ethyl, flumetsulam, flumezin, flumiclorac-pentyl, flumioxazin, flumipropyn, fluometuron, fluorodifen, fluoroglycofen, fluoromidine, fluoronitrofen, fluothiuron, flupoxam, flupropacil, flupropanate, flupyrsulfuron, fluridone, fluorochloridone, fluoroxypyr, fluoroxypyr-meptyl, flurtamone, fluthiacet, fomesafen, foramsulfuron, fosamine, fumiclorac, furyloxyfen, glufosinate, glufosinate-ammonium, glufosinate-P-ammonium, glyphosate salts and esters, halauxifen, halauxifen-methyl, halosafen, halosulfuron-methyl, haloxydine, haloxyfop-methyl, haloxyfop-P-methyl, hexachloroacetone, hexaflurate, hexazinone, imazamethabenz, imazamox, imazapic, imazapyr, imazaquin, imazosulfuron, imazethapyr, indanofan, indaziflam, iodobonil, iodomethane, iodosulfuron, iodosulfuron-ethyl-sodium, iofensulfuron, ioxynil, ipazine, ipfencarbazone, iprymidam, isocarbamid, isocil, isomethiozin, isonoruron, isopolinate, isopropalin, isoproturon, isouron, isoxaben, isoxachlortole, isoxaflutole, isoxapyrifop, karbutilate, ketospiradox, lactofen, lenacil, linuron, MAA, MAMA, MCPA esters and amines, MCPA-thioethyl, MCPB, mecoprop, mecoprop-P, medinoterb, mefenacet, mefluidide, mesoprazine, mesosulfuron, mesotrione, metam, metamifop, metamitron, metazachlor, metazosulfuron, metflurazon, methabenzthiazuron, methalpropalin, methazole, methiobencarb, methiozolin, methiuron, methometon, methoprotryne, methyl bromide, methyl isothiocyanate, methyldymron, metobenzuron, metobromuron, metolachlor, metosulam, metoxuron, metribuzin, metsulfuron, metsulfuron-methyl, molinate, monalide, monisouron, monochloroacetic acid, monolinuron, monuron, morfamquat, MSMA, napronamide, napropamide, naptalam, neburon, nicosulfuron, nipyraclofen, nitralin, nitrofen, nitrofluorfen, norflurazon, noruron, OCH, orbencarb, ortho-dichlorobenzene, orthosulfamuron, oryzalin, oxadiargyl, oxadiazon, oxapyrazon, oxasulfuron, oxaziclomefone, oxyfluorfen, paraflufenethyl, parafluoron, paraquat, pebulate, pelargonic acid, pendimethalin, penoxsulam, pentachlorophenol, pentanochlor, pentoxazone, perfluidone, pethoxamid, phenisopham, phenmedipham, phenmedipham-ethyl, phenobenzuron, phenylmercury acetate, picloram, picolinafen, pinoxaden, piperophos, potassium arsenite, potassium azide, potassium cyanate, pretilachlor, primisulfuron-methyl, procyazine, prodiamine, profluazol, profluralin, profoxydim, proglinazine, prohexadione-calcium, prometon, prometryn, pronamide, propachlor, propanil, propaquizafop, propazine, propham, propisochlor, propoxycarbazone, propyrisulfuron, propyzamide, prosulfalin, prosulfocarb, prosulfuron, proxan, prynachlor, pydanon, pyraclonil, pyraflufen-ethyl, pyrasulfotole, pyrazogyl, pyrazolynate, pyrazosulfuron-ethyl, pyrazoxyfen, pyribenzoxim, pyributicarb, pyriclor, pyridafol, pyridate, pyriftalid, pyriminobac-methyl, pyrimisulfan, pyrithiobac-sodium, pyroxasulfone, pyroxsulam, quinclorac, quinmerac, quinoclamine, quinonamid, quizalofop, quizalofop-P-ethyl, rhodethanil, rimsulfuron, saflufenacil, S-metolachlor, sebuthylazine, secbumeton, sethoxydim, siduron, simazine, simeton, simetryn, SMA, sodium arsenite, sodium azide, sodium chlorate, sulcotrione, sulfallate, sulfentrazone, sulfometuron, sulfosate, sulfosulfuron, sulfuric acid, sulglycapin, swep, SYN-523, TCA, tebutam, tebuthiuron, tefuryltrione, tembotrione, tepraloxydim, terbacil, terbucarb, terbuchlor, terbumeton, terbuthylazine, terbutryn, tetrafluoron, thenylchlor, thiazafluoron, thiazopyr, thidiazimin, thidiazuron, thiencarbazone-methyl, thifensulfuron, thifensulfurn-methyl, thiobencarb, tiocarbazil, tioclorim, topramezone, tralkoxydim, triafamone, tri-allate, triasulfuron, triaziflam, tribenuron, tribenuron-methyl, tricamba, triclopyr choline salt, triclopyr esters and amines, tridiphane, trietazine, trifloxysulfuron, trifluralin, triflusulfuron, trifop, trifopsime, trihydroxytriazine, trimeturon, tripropindan, tritac tritosulfuron, vernolate, xylachlor and salts, esters, optically active isomers and mixtures thereof.

The compositions and methods described herein, can further be used in conjunction with glyphosate, 5-enolpyruvylshikimate-3-phosphate (EPSP) synthase inhibitors, glufosinate, glutamine synthetase inhibitors, dicamba, phenoxy carboxylic acid auxins, pyridine carboxylic acid auxins, pyridyloxy carboxylic auxins, synthetic auxins, auxin transport inhibitors, aryloxyphenoxypropionates, cyclohexanediones, phenylpyrazolines, acetyl CoA carboxylase (ACCase) inhibitors, imidazolinones, sulfonylureas, pyrimidinylthiobenzoates, triazolopyrimidines, sulfonylaminocarbonyltriazolinones, acetolactate synthase (ALS) or acetohydroxy acid synthase (AHAS) inhibitors, 4-hydroxyphenyl-pyruvate dioxygenase (HPPD) inhibitors, phytoene desaturase inhibitors, carotenoid biosynthesis inhibitors, protoporphyrinogen oxidase (PPO) inhibitors, cellulose biosynthesis inhibitors, mitosis inhibitors, microtubule inhibitors, very long chain fatty acid inhibitors, fatty acid and lipid biosynthesis inhibitors, photosystem I inhibitors, photosystem II inhibitors, triazines, and bromoxynil on glyphosate-tolerant, EPSP synthase inhibitor-tolerant, glufosinate-tolerant, glutamine synthetase inhibitor-tolerant, dicamba-tolerant, phenoxy carboxylic acid auxin-tolerant, pyridine carboxylic acid auxin-tolerant, pyridyloxy carboxylic acid auxin-tolerant, auxin-tolerant, auxin transport inhibitor-tolerant, aryloxyphenoxypropionate-tolerant, cyclohexanedione-tolerant, phenylpyrazoline-tolerant, ACCase-tolerant, imidazolinone-tolerant, sulfonylurea-tolerant, pyrimidinylthiobenzoate-tolerant, triazolopyrimidine-tolerant, sulfonylaminocarbonyltriazolinone-tolerant, ALS- or AHAS-tolerant, HPPD-tolerant, phytoene desaturase inhibitor-tolerant, carotenoid biosynthesis inhibitor tolerant, PPO-tolerant, cellulose biosynthesis inhibitor-tolerant, mitosis inhibitor-tolerant, microtubule inhibitor-tolerant, very long chain fatty acid inhibitor-tolerant, fatty acid and lipid biosynthesis inhibitor-tolerant, photosystem I inhibitor-tolerant, photosystem II inhibitor-tolerant, triazine-tolerant, bromoxynil-tolerant, and crops possessing multiple or stacked traits conferring tolerance to multiple chemistries and/or multiple modes of action via single and/or multiple resistance mechanisms. In some embodiments, the compound of formula (I) or salt or ester thereof and complementary herbicide or salt or ester thereof are used in combination with herbicides that are selective for the crop being treated and which complement the spectrum of weeds controlled by these compounds at the application rate employed. In some embodiments, the compositions described herein and other complementary herbicides are applied at the same time, either as a combination formulation, as a tank mix, or as a sequential application.

In some embodiments, the compositions described herein are employed in combination with one or more herbicide safeners, such as AD-67 (MON 4660), benoxacor, benthiocarb, brassinolide, cloquintocet (mexyl), cyometrinil, daimuron, dichlormid, dicyclonon, dimepiperate, disulfoton, fenchlorazole-ethyl, fenclorim, flurazole, fluxofenim, furilazole, harpin proteins, isoxadifen-ethyl, jiecaowan, jiecaoxi, mefenpyr-diethyl, mephenate, naphthalic anhydride (NA), oxabetrinil, R29148 and N-phenyl-sulfonylbenzoic acid amides, to enhance their selectivity. In some embodiments, the safeners are employed in rice, cereal, corn, or maize settings. In some embodiments, the safener is cloquintocet or an ester or salt thereof. In certain embodiments, cloquintocet is utilized to antagonize harmful effects of the compositions on rice and cereals. In some embodiments, the safener is cloquintocet (mexyl).

In some embodiments, the compositions described herein are employed in combination with one or more plant growth regulators, such as 2,3,5-tri-iodobenzoic acid, IAA, IBA, naphthaleneacetamide, α-naphthaleneacetic acids, benzyladenine, 4-hydroxyphenethyl alcohol, kinetin, zeatin, endothal, ethephon, pentachlorophenol, thidiazuron, tribufos, aviglycine, maleic hydrazide, gibberellins, gibberellic acid, abscisic acid, ancymidol, fosamine, glyphosine, isopyrimol, jasmonic acid, maleic hydrazide, mepiquat, 2,3,5-tri-iodobenzoic acid, morphactins, dichlorflurenol, flurprimidol, mefluidide, paclobutrazol, tetcyclacis, uniconazole, brassinolide, brassinolide-ethyl, cycloheximide, ethylene, methasulfocarb, prohexadione, triapenthenol and trinexapac.

In some embodiments, the plant growth regulators are employed in one or more crops or settings, such as rice, cereal crops, corn, maize, broadleaf crops, oilseed rape/canola, turf, pineapple, sugarcane, sunflower, pastures, grasslands, rangelands, fallowland, tree and vine orchards, plantation crops, vegetables, and non-crop (ornamentals) settings. In some embodiments, the plant growth regulator is mixed with the compound of formula (I), or mixed with the compound of formula (I) and an insecticide to cause a preferentially advantageous effect on plants.

In some embodiments, compositions provided herein further comprise at least one agriculturally acceptable adjuvant or carrier. Suitable adjuvants or carriers should not be phytotoxic to valuable crops, particularly at the concentrations employed in applying the compositions for selective weed control in the presence of crops, and should not react chemically with herbicidal components or other composition ingredients. Such mixtures can be designed for application directly to weeds or the area adjacent to the weeds or can be concentrates or formulations that are normally diluted with additional carriers and adjuvants before application. They can be solids, such as, for example, dusts, granules, water-dispersible granules, or wettable powders, or liquids, such as, for example, emulsifiable concentrates, solutions, emulsions or suspensions. They can also be provided as a pre-mix or tank mixed.

Suitable agricultural adjuvants and carriers include, but are not limited to, crop oil concentrate; nonylphenol ethoxylate; benzylcocoalkyldimethyl quaternary ammonium salt; blend of petroleum hydrocarbon, alkyl esters, organic acid, and anionic surfactant; $C_9$-$C_{11}$ alkylpolyglycoside; phosphated alcohol ethoxylate; natural primary alcohol ($C_{12}$-$C_{16}$) ethoxylate; di-sec-butylphenol EO-PO block copolymer; polysiloxane-methyl cap; nonylphenol ethoxylate+urea ammonium nitrate; emulsified methylated seed oil; tridecyl alcohol (synthetic) ethoxylate (8EO); tallow amine ethoxylate (15 EO); PEG(400) dioleate-99.

Liquid carriers that can be employed include water and organic solvents. The organic solvents include, but are not limited to, petroleum fractions or hydrocarbons such as mineral oil, aromatic solvents, paraffinic oils, and the like; vegetable oils such as soybean oil, rapeseed oil, olive oil, castor oil, sunflower seed oil, coconut oil, corn oil, cottonseed oil, linseed oil, palm oil, peanut oil, safflower oil, sesame oil, tung oil and the like; esters of the above vegetable oils; esters of monoalcohols or dihydric, trihydric, or other lower polyalcohols (4-6 hydroxy containing), such as 2-ethyl hexyl stearate, n-butyl oleate, isopropyl myristate, propylene glycol dioleate, di-octyl succinate, di-butyl adipate, di-octyl phthalate and the like; esters of mono, di and polycarboxylic acids and the like. Specific organic solvents include, but are not limited to toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methyl alcohol, ethyl alcohol, isopropyl alcohol, amyl alcohol, ethylene glycol, propylene glycol, glycerine, N-methyl-2-pyrrolidinone, N,N-dimethyl alkylamides, dimethyl sulfoxide, liquid fertilizers and the like. In certain embodiments, water is the carrier for the dilution of concentrates.

Suitable solid carriers include but are not limited to talc, pyrophyllite clay, silica, attapulgus clay, kaolin clay, kieselguhr, chalk, diatomaceous earth, lime, calcium carbonate, bentonite clay, Fuller's earth, cottonseed hulls, wheat flour, soybean flour, pumice, wood flour, walnut shell flour, lignin, cellulose, and the like.

In some embodiments, the compositions described herein further comprise one or more surface-active agents. In some embodiments, such surface-active agents are employed in both solid and liquid compositions, and in certain embodiments those designed to be diluted with carrier before application. The surface-active agents can be anionic, cationic or nonionic in character and can be employed as emulsifying agents, wetting agents, suspending agents, or for other purposes. Surfactants which may also be used in the present formulations are described, inter alia, in "McCutcheon's Detergents and Emulsifiers Annual," MC Publishing Corp., Ridgewood, N.J., 1998 and in "Encyclopedia of Surfactants," Vol. I-III, Chemical Publishing Co., New York, 1980-81. Surface-active agents include, but are not limited to salts of alkyl sulfates, such as diethanolammonium lauryl sulfate; alkylarylsulfonate salts, such as calcium dodecylbenzenesulfonate; alkylphenol-alkylene oxide addition products, such as nonylphenol-$C_{18}$ ethoxylate; alcohol-alkylene oxide addition products, such as tridecyl alcohol-$C_{16}$ ethoxylate; soaps, such as sodium stearate; alkylnaphthalene-sulfonate salts, such as sodium dibutylnaphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; salts of mono and dialkyl phosphate esters; vegetable or seed oils such as soybean oil, rapeseed/canola oil, olive oil, castor oil, sunflower seed oil, coconut oil, corn oil, cottonseed oil, linseed oil, palm oil, peanut oil, safflower oil, sesame oil, tung oil and the like; and esters of the above vegetable oils, and in certain embodiments, methyl esters.

In some embodiments, these materials, such as vegetable or seed oils and their esters, can be used interchangeably as an agricultural adjuvant, as a liquid carrier or as a surface active agent.

Other exemplary additives for use in the compositions provided herein include but are not limited to compatibilizing agents, antifoam agents, sequestering agents, neutralizing agents and buffers, corrosion inhibitors, dyes, odorants, spreading agents, penetration aids, sticking agents, dispersing agents, thickening agents, freezing point depressants, antimicrobial agents, and the like. The compositions may also contain other compatible components, for example, other herbicides, plant growth regulators, fungicides, insecticides, and the like and can be formulated with liquid fertilizers or solid, particulate fertilizer carriers such as ammonium nitrate, urea and the like.

In some embodiments, the concentration of the active ingredients in the compositions described herein is from about 0.0005 to 98 percent by weight. In some embodiments, the concentration is from about 0.0006 to 90 percent by weight. In compositions designed to be employed as concentrates, the active ingredients, in certain embodiments, are present in a concentration from about 0.1 to 98 weight percent, and in certain embodiment's about 0.5 to 90 weight percent. Such compositions are, in certain embodiments, diluted with an inert carrier, such as water, before application. The diluted compositions usually applied to weeds or the locus of weeds contain, in certain embodiments, about 0.0006 to 15.0 weight percent active ingredient and in certain embodiments contain about 0.01 to 10.0 weight percent.

The present compositions can be applied to undesirable vegetation (weeds) or the area adjacent to the weeds by the use of conventional ground or aerial dusters, sprayers, and granule applicators, by addition to irrigation or paddy water, and by other conventional means known to those skilled in the art.

The described embodiments and following examples are for illustrative purposes and are not intended to limit the scope of the claims. Other modifications, uses, or combinations with respect to the compositions described herein will be apparent to a person of ordinary skill in the art without departing from the spirit and scope of the claimed subject matter.

EXAMPLES

Results in Examples I and II are greenhouse trial results.

Example I

Evaluation of Postemergence Foliar-Applied Herbicidal Mixtures for Weed Control in Direct-Seeded Rice Seeds or nutlets of the desired test plant species were planted in a soil matrix prepared by mixing a loam or sandy loam soil (e.g., 28.6 percent silt, 18.8 percent clay, and 52.6 percent sand, with a pH of about 5.8 and an organic matter content of about 1.8 percent) and calcareous grit in an 80 to 20 ratio. The soil matrix was contained in plastic pots with a volume of 1 quart and a surface area of 83.6 square centimeters ($cm^2$). When required to ensure good germination and healthy plants, a fungicide treatment and/or other chemical or physical treatment was applied. The plants were grown for 8-22 days in a greenhouse with an approximate 14 hour (h) photoperiod which was maintained at about 29° C. during the day and 26° C. during the night. Nutrients (Peters Excel® 15-5-15 5-Ca 2-Mg and iron chelate) were applied in the irrigation solution as needed and water was added on a regular basis. Supplemental lighting was provided with overhead metal halide 1000-Watt lamps as necessary. The plants were employed for testing when they reached the first through fourth true leaf stage.

Treatments consisted of the acid or esters of 4-amino-3-chloro-6-(4-chloro-2-fluoro-3-methoxyphenyl)-5-fluoropyridine-2-carboxylic acid (Compound A), each formulated as an SC (suspension concentrate), and various insecticidal components alone and in combination. Forms of compound A were applied on an acid equivalent basis.

Forms of compound A (compound of formula I) tested include:

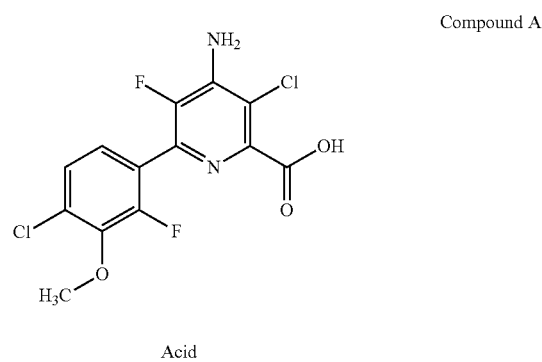

Compound A

Acid

-continued

Compound A

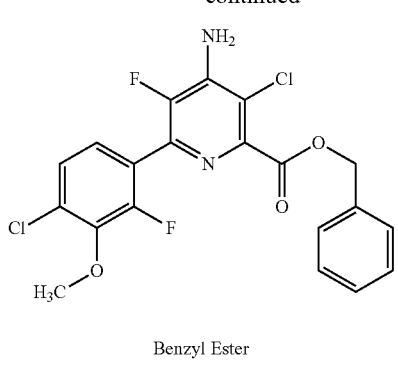

Benzyl Ester

Other insecticidal components were applied on an active ingredient basis and consisted of acephate formulated as Acephate 97UP, carbaryl formulated as Sevin SL, carbofuran (technical grade material), cartap hydrochloride (technical grade material), chlorpyrifos (technical grade material), chlorpyrifos formulated as Dursban 75WG, cypermethrin formulated as Demon WP, dimethoate (technical grade material), fipronil (technical grade material), etofenprox (technical grade material), imidacloprid (technical grade material), lambda-cyhalothrin (technical grade material), malathion formulated as Malathion 57EC, piperonyl butoxide formulated as Incite, spinetoram (technical grade material), spinosad formulated as Spinosad 240 SC, sulfoxaflor formulated as Sulfoxaflor WG, or triazophos (technical grade material).

Treatment requirements were calculated based upon the rates being tested, the concentration of active ingredient or acid equivalent in the formulation, and a 12 milliliter (mL) application volume at a rate of 187 liters per hectare (L/ha).

For treatments comprised of formulated compounds, measured amounts of compounds were placed individually in 25 mL glass vials and diluted in a volume of 1.25% volume per volume (v/v) Agri-Dex® crop oil concentrate to obtain 12× stock solutions. If a test compound did not dissolve readily, the mixture was warmed and/or sonicated. Application solutions were prepared by adding an appropriate amount of each stock solution (e.g., 1 mL) and diluted to the appropriate final concentrations with the addition of 10 mL of an aqueous mixture of 1.25% (v/v) crop oil concentrate so that the final spray solutions contained 1.25+/−0.05% (v/v) crop oil concentrate.

For treatments comprised of formulated and technical compounds, weighed amounts of the technical materials were placed individually in 25 mL glass vials and dissolved in a volume of 97:3 v/v acetone/DMSO to obtain 12× stock solutions, and measured amounts of the formulated compounds were placed individually in 25 mL glass vials and diluted in a volume of 1.5% (v/v) crop oil concentrate or water to obtain 12× stock solutions. If a test compound did not dissolve readily, the mixture was warmed and/or sonicated. Application solutions were prepared by adding an appropriate amount of each stock solution (e.g., 1 mL) and diluted to the appropriate final concentrations with the addition of an appropriate amount of an aqueous mixture of 1.5% (v/v) crop oil concentrate so that the final spray solutions contained 1.25% (v/v) crop oil concentrate. As required, additional water and/or 97:3 v/v acetone/DMSO was added to individual application solutions so that the final acetone and DMSO concentrations of the application solutions being compared were 8.1% and 0.25%, respectively.

All stock solutions and applications solutions were visually inspected for compound compatibility prior to application. Spray solutions were applied to the plant material with an overhead Mandel track sprayer equipped with 8002E nozzles calibrated to deliver 187 L/ha over an application area of 0.503 square meters ($m^2$) at a spray height of 18 to 20 inches (46 to 50 cm) above average plant canopy height. Control plants were sprayed in the same manner with the solvent blank.

The treated plants and control plants were placed in a greenhouse as described above and watered by sub-irrigation to prevent wash-off of the test compounds. After approximately 3 weeks, the condition of the test plants as compared to that of the untreated plants was determined visually and scored on a scale of 0 to 100 percent where 0 corresponds to no injury or growth inhibition and 100 corresponds to complete kill.

Colby's equation was used to determine the herbicidal effects expected from the mixtures (Colby, S. R. Calculation of the synergistic and antagonistic response of herbicide combinations. *Weeds* 1967, 15, 20-22.).

The following equation was used to calculate the expected activity of mixtures containing two active ingredients, A and B:

$$\text{Expected} = A + B - (A \times B / 100)$$

A=observed efficacy of active ingredient A at the same concentration as used in the mixture;

B=observed efficacy of active ingredient B at the same concentration as used in the mixture.

The compounds tested, application rates employed, plant species tested, and results are given in Tables 1-24.

TABLE 1

Synergistic Activity of Foliar-Applied Compound A Benzyl Ester and Acephate Compositions on Weed Control in a Rice Cropping System.

| Compound A Benzyl Ester | Acephate | Visual Weed Control (%) - 21 DAA BRAPP | |
|---|---|---|---|
| g ae/ha | g ai/ha | Obs | Exp |
| 8 | 0 | 70 | — |
| 0 | 140 | 0 | — |
| 0 | 280 | 0 | — |
| 0 | 560 | 0 | — |
| 8 | 140 | 80 | 70 |
| 8 | 280 | 70 | 70 |
| 8 | 560 | 90 | 70 |

| Compound A Benzyl Ester | Acephate | Visual Weed Control (%) - 21 DAA IPOHE | |
|---|---|---|---|
| g ae/ha | g ai/ha | Obs | Exp |
| 8 | 0 | 10 | — |
| 16 | 0 | 50 | — |
| 32 | 0 | 60 | — |
| 0 | 280 | 10 | — |
| 8 | 280 | 25 | 19 |
| 16 | 280 | 95 | 55 |
| 32 | 280 | 70 | 64 |

| Compound A Benzyl Ester | Acephate | Visual Weed Control (%) - 21 DAA CYPIR | |
|---|---|---|---|
| g ae/ha | g ai/ha | Obs | Exp |
| 8 | 0 | 50 | — |
| 0 | 140 | 0 | — |
| 0 | 280 | 0 | — |
| 0 | 560 | 0 | — |

TABLE 1-continued

Synergistic Activity of Foliar-Applied Compound A Benzyl Ester and Acephate Compositions on Weed Control in a Rice Cropping System.

| | | | |
|---|---|---|---|
| 8 | 140 | 70 | 50 |
| 8 | 280 | 75 | 50 |
| 8 | 560 | 60 | 50 |

TABLE 2

Synergistic Activity of Foliar-Applied Compound A Acid and Carbaryl Compositions on Weed Control in a Rice Cropping System.

| Compound A Acid | Carbaryl | Visual Weed Control (%) - 20 DAA | | | | | | | |
|---|---|---|---|---|---|---|---|---|---|
| | | BRAPP | | DIGSA | | LEFCH | | CYPIR | |
| g ae/ha | g ai/ha | Obs | Exp | Obs | Exp | Obs | Exp | Obs | Exp |
| 4.38 | 0 | 70 | — | 40 | — | 0 | — | 30 | — |
| 0 | 3 | 0 | — | 0 | — | 0 | — | 0 | — |
| 0 | 6 | 0 | — | 0 | — | 0 | — | 0 | — |
| 0 | 12 | 0 | — | 0 | — | 0 | — | 0 | — |
| 4.38 | 3 | 90 | 70 | 55 | 40 | 15 | 0 | 85 | 30 |
| 4.38 | 6 | 90 | 70 | 55 | 40 | 15 | 0 | 65 | 30 |
| 4.38 | 12 | 80 | 70 | 40 | 40 | 30 | 0 | 80 | 30 |

| Compound A Acid | Carbaryl | Visual Weed Control (%) - 20 DAA ECHCG | |
|---|---|---|---|
| g ae/ha | g ai/ha | Obs | Exp |
| 4.38 | 0 | 60 | — |
| 8.75 | 0 | 80 | — |
| 17.5 | 0 | 95 | — |
| 0 | 3 | 0 | — |
| 0 | 6 | 0 | — |
| 0 | 12 | 0 | — |
| 4.38 | 3 | 85 | 60 |
| 8.75 | 3 | 95 | 80 |
| 17.5 | 3 | 95 | 95 |
| 4.38 | 6 | 80 | 60 |
| 8.75 | 6 | 95 | 80 |
| 17.5 | 6 | 99 | 95 |
| 4.38 | 12 | 70 | 60 |
| 8.75 | 12 | 95 | 80 |
| 17.5 | 12 | 99 | 95 |

TABLE 3

Synergistic Activity of Foliar-Applied Compound A Benzyl Ester and Carbaryl Compositions on Weed Control in a Rice Cropping System.

| Compound A Benzyl Ester | Carbaryl | Visual Weed Control (%) - 20 DAA | | | |
|---|---|---|---|---|---|
| | | DIGSA | | IPOHE | |
| g ae/ha | g ai/ha | Obs | Exp | Obs | Exp |
| 4.38 | 0 | 40 | — | 10 | — |
| 8.75 | 0 | 40 | — | 15 | — |
| 0 | 6 | 0 | — | 0 | — |
| 0 | 12 | 0 | — | 10 | — |
| 4.38 | 6 | 40 | 40 | 20 | 10 |
| 8.75 | 6 | 70 | 40 | 20 | 15 |
| 4.38 | 12 | 50 | 40 | 40 | 19 |
| 8.75 | 12 | 65 | 40 | 25 | 24 |

| Compound A Benzyl Ester | Carbaryl | Visual Weed Control (%) - 20 DAA | | | |
|---|---|---|---|---|---|
| | | ECHCG | | LEFCH | |
| g ae/ha | g ai/ha | Obs | Exp | Obs | Exp |
| 4.38 | 0 | 60 | — | 15 | — |
| 8.75 | 0 | 85 | — | 30 | — |
| 17.5 | 0 | 90 | — | 50 | — |
| 0 | 3 | 0 | — | 0 | — |
| 0 | 6 | 0 | — | 0 | — |
| 0 | 12 | 0 | — | 0 | — |
| 4.38 | 3 | 90 | 60 | 35 | 15 |
| 8.75 | 3 | 90 | 85 | 30 | 30 |
| 17.5 | 3 | 99 | 90 | 70 | 50 |
| 4.38 | 6 | 95 | 60 | 25 | 15 |
| 8.75 | 6 | 95 | 85 | 35 | 30 |
| 17.5 | 6 | 99 | 90 | 65 | 50 |
| 4.38 | 12 | 85 | 60 | 15 | 15 |
| 8.75 | 12 | 99 | 85 | 50 | 30 |
| 17.5 | 12 | 99 | 90 | 80 | 50 |

| Compound A Benzyl Ester | Carbaryl | Visual Weed Control (%) - 20 DAA DIGSA | |
|---|---|---|---|
| g ae/ha | g ai/ha | Obs | Exp |
| 16 | 0 | 23 | — |
| 32 | 0 | 30 | — |
| 0 | 24 | 0 | — |
| 0 | 48 | 0 | — |
| 0 | 96 | 0 | — |
| 16 | 24 | 40 | 23 |
| 32 | 24 | 40 | 30 |
| 16 | 48 | 30 | 23 |
| 32 | 48 | 45 | 30 |
| 16 | 96 | 55 | 23 |
| 32 | 96 | 45 | 30 |

| Compound A Benzyl Ester | Carbaryl | Visual Weed Control (%) - 20 DAA CYPES | |
|---|---|---|---|
| g ae/ha | g ai/ha | Obs | Exp |
| 32 | 0 | 73 | — |
| 0 | 24 | 0 | — |
| 0 | 48 | 0 | — |
| 0 | 96 | 0 | — |
| 32 | 24 | 100 | 73 |
| 32 | 48 | 70 | 73 |
| 32 | 96 | 100 | 73 |

TABLE 4

Synergistic Activity of Foliar-Applied Compound A Acid and Carbofuran Compositions on Weed Control in a Rice Cropping System.

| Compound A Acid g ae/ha | Carbofuran g ai/ha | Visual Weed Control (%) - 21 DAA IPOHE | |
|---|---|---|---|
| | | Obs | Exp |
| 5.3 | 0 | 10 | — |
| 10.6 | 0 | 10 | — |
| 21.2 | 0 | 25 | — |
| 0 | 500 | 0 | — |
| 5.3 | 500 | 20 | 10 |
| 10.6 | 500 | 15 | 10 |
| 21.2 | 500 | 50 | 25 |

TABLE 5

Synergistic Activity of Foliar-Applied Compound A Benzyl Ester and Carbofuran Compositions on Weed Control in a Rice Cropping System.

| Compound A Benzyl Ester g ae/ha | Carbofuran g ai/ha | Visual Weed Control (%) - 21 DAA LEFCH | |
|---|---|---|---|
| | | Obs | Exp |
| 4.38 | 0 | 10 | — |
| 8.75 | 0 | 25 | — |
| 17.5 | 0 | 30 | — |
| 0 | 500 | 0 | — |
| 4.38 | 500 | 25 | 10 |
| 8.75 | 500 | 20 | 25 |
| 17.5 | 500 | 35 | 30 |

| Compound A Benzyl Ester g ae/ha | Carbofuran g ai/ha | Visual Weed Control (%) - 20 DAA CYPES | |
|---|---|---|---|
| | | Obs | Exp |
| 8 | 0 | 25 | — |
| 16 | 0 | 40 | — |
| 0 | 125 | 0 | — |
| 0 | 250 | 0 | — |
| 8 | 125 | 60 | 25 |
| 16 | 125 | 70 | 40 |
| 8 | 250 | 75 | 25 |

TABLE 6

Synergistic Activity of Foliar-Applied Compound A Benzyl Ester and Cartap Hydrochloride Compositions on Weed Control in a Rice Cropping System.

| Compound A Benzyl Ester g ae/ha | Cartap Hydrochloride g ai/ha | Visual Weed Control (%) - 22 DAA ECHCG | |
|---|---|---|---|
| | | Obs | Exp |
| 8 | 0 | 50 | — |
| 16 | 0 | 60 | — |
| 0 | 250 | 0 | — |
| 0 | 500 | 0 | — |
| 8 | 250 | 60 | 50 |
| 16 | 250 | 75 | 60 |
| 8 | 500 | 70 | 50 |
| 16 | 500 | 95 | 60 |

| Compound A Benzyl Ester g ae/ha | Cartap Hydrochloride g ai/ha | Visual Weed Control (%) - 22 DAA LEFCH | |
|---|---|---|---|
| | | Obs | Exp |
| 8 | 0 | 25 | — |
| 16 | 0 | 30 | — |
| 32 | 0 | 60 | — |
| 0 | 250 | 0 | — |
| 0 | 500 | 0 | — |
| 8 | 250 | 40 | 25 |
| 16 | 250 | 35 | 30 |
| 32 | 250 | 65 | 60 |
| 8 | 500 | 30 | 25 |
| 16 | 500 | 60 | 30 |
| 32 | 500 | 65 | 60 |

| Compound A Benzyl Ester g ae/ha | Cartap Hydrochloride g ai/ha | Visual Weed Control (%) - 22 DAA IPOHE | |
|---|---|---|---|
| | | Obs | Exp |
| 16 | 0 | 10 | — |
| 32 | 0 | 35 | — |
| 0 | 250 | 10 | — |
| 0 | 500 | 0 | — |
| 16 | 250 | 30 | 19 |
| 32 | 250 | 50 | 42 |
| 16 | 500 | 25 | 10 |
| 32 | 500 | 45 | 35 |

TABLE 7

Synergistic Activity of Foliar-Applied Compound A Acid and Chlorpyrifos Compositions on Weed Control in a Rice Cropping System.

| Compound A Acid g ae/ha | Chlorpyrifos g ai/ha | Visual Weed Control (%) - 20 DAA | | | |
|---|---|---|---|---|---|
| | | DIGSA | | LEFCH | |
| | | Obs | Exp | Obs | Exp |
| 5.3 | 0 | 15 | — | 0 | — |
| 10.6 | 0 | 35 | — | 20 | — |
| 21.2 | 0 | 50 | — | 45 | — |
| 0 | 500 | 0 | — | 0 | — |
| 5.3 | 500 | 40 | 15 | 20 | 0 |
| 10.6 | 500 | 25 | 35 | 35 | 20 |
| 21.2 | 500 | 75 | 50 | 50 | 45 |

TABLE 8

Synergistic Activity of Foliar-Applied Compound A Benzyl Ester and Chlorpyrifos Compositions on Weed Control in a Rice Cropping System.

| Compound A Benzyl Ester g ae/ha | Chlorpyrifos g ai/ha | Visual Weed Control (%) - 20 DAA | | | |
|---|---|---|---|---|---|
| | | DIGSA | | LEFCH | |
| | | Obs | Exp | Obs | Exp |
| 4.38 | 0 | 25 | — | 20 | — |
| 8.75 | 0 | 10 | — | 35 | — |

TABLE 8-continued

Synergistic Activity of Foliar-Applied Compound A Benzyl Ester and Chlorpyrifos Compositions on Weed Control in a Rice Cropping System.

| 17.5 | 0 | 15 | — | 60 | — |
|---|---|---|---|---|---|
| 0 | 500 | 0 | — | 0 | — |
| 4.38 | 500 | 40 | 25 | 20 | 20 |
| 8.75 | 500 | 25 | 10 | 45 | 35 |
| 17.5 | 500 | 25 | 15 | 75 | 60 |

| Compound A Benzyl Ester | Chlorpyrifos | Visual Weed Control (%) - 20 DAA | | | | |
|---|---|---|---|---|---|---|
| | | BRAPP | | ECHCG | | ECHCO |
| g ae/ha | g ai/ha | Obs | Exp | Obs | Exp | Obs | Exp |
| 8 | 0 | 55 | — | 70 | — | 65 | — |
| 0 | 180 | 0 | — | 0 | — | 0 | — |
| 0 | 360 | 0 | — | 0 | — | 0 | — |
| 0 | 720 | 0 | — | 0 | — | 0 | — |
| 8 | 180 | 80 | 55 | 85 | 70 | 85 | 65 |
| 8 | 360 | 80 | 55 | 90 | 70 | 80 | 65 |
| 8 | 720 | 80 | 55 | 90 | 70 | 85 | 65 |

| Compound A Benzyl Ester | Chlorpyrifos | Visual Weed Control (%) - 20 DAA | | | | |
|---|---|---|---|---|---|---|
| | | DIGSA | | LEFCH | | IPOHE |
| g ae/ha | g ai/ha | Obs | Exp | Obs | Exp | Obs | Exp |
| 8 | 0 | 20 | — | 15 | — | 10 | — |
| 16 | 0 | 30 | — | 25 | — | 40 | — |
| 32 | 0 | 40 | — | 30 | — | 50 | — |
| 0 | 180 | 0 | — | 0 | — | 10 | — |
| 0 | 360 | 0 | — | 0 | — | 10 | — |
| 0 | 720 | 0 | — | 0 | — | 0 | — |
| 8 | 180 | 60 | 20 | 20 | 15 | 50 | 19 |
| 16 | 180 | 65 | 30 | 65 | 25 | 65 | 46 |
| 32 | 180 | 70 | 40 | 35 | 30 | 65 | 55 |
| 8 | 360 | 60 | 20 | 20 | 15 | 55 | 19 |
| 16 | 360 | 70 | 30 | 45 | 25 | 55 | 46 |
| 32 | 360 | 65 | 40 | 65 | 30 | 65 | 55 |
| 8 | 720 | 65 | 20 | 25 | 15 | 35 | 10 |
| 16 | 720 | 75 | 30 | 50 | 25 | 50 | 40 |
| 32 | 720 | 80 | 40 | 65 | 30 | 65 | 50 |

| Compound A Benzyl Ester | Chlorpyrifos | Visual Weed Control (%) - 22 DAA | | | | |
|---|---|---|---|---|---|---|
| | | DIGSA | | LEFCH | | LEFFA |
| g ae/ha | g ai/ha | Obs | Exp | Obs | Exp | Obs | Exp |
| 8 | 0 | 13 | — | 18 | — | 23 | — |
| 16 | 0 | 18 | — | 43 | — | 30 | — |
| 32 | 0 | 28 | — | 53 | — | 45 | — |
| 0 | 180 | 0 | — | 0 | — | 0 | — |
| 0 | 360 | 0 | — | 0 | — | 0 | — |
| 0 | 720 | 0 | — | 5 | — | 0 | — |
| 8 | 180 | 40 | 13 | 38 | 18 | 25 | 23 |
| 16 | 180 | 50 | 18 | 45 | 43 | 65 | 30 |
| 32 | 180 | 55 | 28 | 70 | 53 | 68 | 45 |
| 8 | 360 | 53 | 13 | 35 | 18 | 30 | 23 |
| 16 | 360 | 63 | 18 | 43 | 43 | 58 | 30 |
| 32 | 360 | 68 | 28 | 75 | 53 | 80 | 45 |
| 8 | 720 | 55 | 13 | 40 | 22 | 38 | 23 |
| 16 | 720 | 63 | 18 | 73 | 45 | 70 | 30 |
| 32 | 720 | 68 | 28 | 80 | 55 | 78 | 45 |

TABLE 9

Synergistic Activity of Foliar-Applied Compound A Benzyl Ester and Cypermethrin Compositions on Weed Control in a Rice Cropping System.

| Compound A Benzyl Ester | Cypermethrin | Visual Weed Control (%) - 22 DAA ECHCG | |
|---|---|---|---|
| g ae/ha | g ai/ha | Obs | Exp |
| 8 | 0 | 50 | — |
| 16 | 0 | 60 | — |
| 0 | 7.5 | 0 | — |
| 0 | 22.5 | 0 | — |
| 0 | 60 | 0 | — |
| 8 | 7.5 | 60 | 50 |
| 16 | 7.5 | 70 | 60 |
| 8 | 22.5 | 60 | 50 |
| 16 | 22.5 | 85 | 60 |
| 8 | 60 | 60 | 50 |
| 16 | 60 | 80 | 60 |

| Compound A Benzyl Ester | Cypermethrin | Visual Weed Control (%) - 22 DAA LEFCH | |
|---|---|---|---|
| g ae/ha | g ai/ha | Obs | Exp |
| 16 | 0 | 30 | — |
| 0 | 7.5 | 0 | — |
| 0 | 22.5 | 0 | — |
| 0 | 60 | 0 | — |
| 16 | 7.5 | 50 | 30 |
| 16 | 22.5 | 60 | 30 |
| 16 | 60 | 35 | 30 |

| Compound A Benzyl Ester | Cypermethrin | Visual Weed Control (%) - 22 DAA IPOHE | |
|---|---|---|---|
| g ae/ha | g ai/ha | Obs | Exp |
| 16 | 0 | 10 | — |
| 32 | 0 | 35 | — |
| 0 | 7.5 | 0 | — |
| 0 | 22.5 | 0 | — |
| 0 | 60 | 0 | — |
| 16 | 7.5 | 25 | 10 |
| 32 | 7.5 | 45 | 35 |
| 16 | 22.5 | 25 | 10 |
| 32 | 22.5 | 45 | 35 |
| 16 | 60 | 10 | 10 |
| 32 | 60 | 45 | 35 |

| Compound A Benzyl Ester | Cypermethrin | Visual Weed Control (%) - 21 DAA DIGSA | |
|---|---|---|---|
| g ae/ha | g ai/ha | Obs | Exp |
| 8 | 0 | 10 | — |
| 0 | 15 | 0 | — |
| 0 | 30 | 0 | — |
| 0 | 60 | 0 | — |
| 8 | 15 | 30 | 10 |
| 8 | 30 | 10 | 10 |
| 8 | 60 | 30 | 10 |

TABLE 10

Synergistic Activity of Foliar-Applied Compound A Acid and Dimethoate Compositions on Weed Control in a Rice Cropping System.

| Compound A Acid | Dimethoate | Visual Weed Control (%) - 22 DAA ECHCO | |
|---|---|---|---|
| g ae/ha | g ai/ha | Obs | Exp |
| 4.38 | 0 | 55 | — |
| 0 | 480 | 10 | — |
| 4.38 | 480 | 70 | 60 |

TABLE 11

Synergistic Activity of Foliar-Applied Compound A Benzyl Ester and Dimethoate Compositions on Weed Control in a Rice Cropping System.

| Compound A Benzyl Ester | Dimethoate | Visual Weed Control (%) - 22 DAA | | | | | |
|---|---|---|---|---|---|---|---|
| | | LEFCH | | CYPIR | | SCPJU | |
| g ae/ha | g ai/ha | Obs | Exp | Obs | Exp | Obs | Exp |
| 4.38 | 0 | 30 | — | 70 | — | 70 | — |
| 0 | 480 | 0 | — | 0 | — | 0 | — |
| 4.38 | 480 | 60 | 30 | 100 | 70 | 100 | 70 |

TABLE 12

Synergistic Activity of Foliar-Applied Compound A Benzyl Ester and Etofenprox Compositions on Weed Control in a Rice Cropping System.

| Compound A Benzyl Ester | Etofenprox | Visual Weed Control (%) - 22 DAA | | | | | |
|---|---|---|---|---|---|---|---|
| | | ECHCG | | LEFCH | | CYPES | |
| g ae/ha | g ai/ha | Obs | Exp | Obs | Exp | Obs | Exp |
| 8 | 0 | 50 | — | 25 | — | 70 | — |
| 16 | 0 | 60 | — | 30 | — | 95 | — |
| 0 | 75 | 0 | — | 0 | — | 0 | — |
| 0 | 150 | 0 | — | 0 | — | 0 | — |
| 8 | 75 | 60 | 50 | 30 | 25 | 95 | 70 |
| 16 | 75 | 80 | 60 | 70 | 30 | 100 | 95 |
| 8 | 150 | 65 | 50 | 40 | 25 | 85 | 70 |
| 16 | 150 | 85 | 60 | 45 | 30 | 100 | 95 |

| Compound A Benzyl Ester | Etofenprox | Visual Weed Control (%) - 19 DAA | | | | | |
|---|---|---|---|---|---|---|---|
| | | ECHCG | | ECHCO | | LEFCH | |
| g ae/ha | g ai/ha | Obs | Exp | Obs | Exp | Obs | Exp |
| 8 | 0 | 85 | — | 65 | — | 45 | — |
| 16 | 0 | 85 | — | 90 | — | 45 | — |
| 32 | 0 | 95 | — | 95 | — | 50 | — |
| 0 | 300 | 0 | — | 0 | — | 0 | — |
| 8 | 300 | 95 | 85 | 95 | 65 | 40 | 45 |
| 16 | 300 | 99 | 85 | 95 | 90 | 70 | 45 |
| 32 | 300 | 100 | 95 | 99 | 95 | 70 | 50 |

| Compound A Benzyl Ester | Etofenprox | Visual Weed Control (%) - 22 DAA IPOHE | |
|---|---|---|---|
| g ae/ha | g ai/ha | Obs | Exp |
| 16 | 0 | 10 | — |
| 32 | 0 | 35 | — |
| 0 | 75 | 0 | — |
| 0 | 150 | 0 | — |
| 16 | 75 | 25 | 10 |
| 32 | 75 | 40 | 35 |
| 16 | 150 | 40 | 10 |
| 32 | 150 | 45 | 35 |

TABLE 13

Synergistic Activity of Foliar-Applied Compound A Acid and Fipronil Compositions on Weed Control in a Rice Cropping System.

| Compound A Acid | Fipronil | Visual Weed Control (%) - 20 DAA ECHCG | |
|---|---|---|---|
| g ae/ha | g ai/ha | Obs | Exp |
| 5.3 | 0 | 65 | — |
| 10.6 | 0 | 90 | — |
| 21.2 | 0 | 95 | — |
| 0 | 50 | 0 | — |
| 5.3 | 50 | 85 | 65 |
| 10.6 | 50 | 95 | 90 |
| 21.2 | 50 | 95 | 95 |

TABLE 14

Synergistic Activity of Foliar-Applied Compound A Benzyl Ester and Fipronil Compositions on Weed Control in a Rice Cropping System.

| Compound A Benzyl Ester | Fipronil | Visual Weed Control (%) - 20 DAA | | | |
|---|---|---|---|---|---|
| | | ECHCG | | BRAPP | |
| g ae/ha | g ai/ha | Obs | Exp | Obs | Exp |
| 4.38 | 0 | 70 | — | 75 | — |
| 8.75 | 0 | 80 | — | 75 | — |
| 17.5 | 0 | 95 | — | 95 | — |
| 0 | 50 | 0 | — | 0 | — |
| 4.38 | 50 | 75 | 70 | 75 | 75 |
| 8.75 | 50 | 90 | 80 | 95 | 75 |
| 17.5 | 50 | 95 | 95 | 95 | 95 |

TABLE 15

Synergistic Activity of Foliar-Applied Compound A Benzyl Ester and Imidacloprid Compositions on Weed Control in a Rice Cropping System.

| Compound A Benzyl Ester | Imidacloprid | Visual Weed Control (%) - 20 DAA | | | |
|---|---|---|---|---|---|
| | | BRAPP | | DIGSA | |
| g ae/ha | g ai/ha | Obs | Exp | Obs | Exp |
| 4.38 | 0 | 75 | — | 25 | — |
| 8.75 | 0 | 75 | — | 10 | — |
| 17.5 | 0 | 95 | — | 15 | — |
| 0 | 500 | 0 | — | 0 | — |
| 4.38 | 500 | 95 | 75 | 15 | 25 |
| 8.75 | 500 | 95 | 75 | 35 | 10 |
| 17.5 | 500 | 99 | 95 | 35 | 15 |

TABLE 16

Synergistic Activity of Foliar-Applied Compound A Acid and Lamba Cyhalothrin Compositions on Weed Control in a Rice Cropping System.

| Compound A Acid | Lambda cyhalothrin | Visual Weed Control (%) - 21 DAA | | | |
|---|---|---|---|---|---|
| | | IPOHE | | ECHCG | |
| g ae/ha | g ai/ha | Obs | Exp | Obs | Exp |
| 5.3 | 0 | 10 | — | 65 | — |
| 10.6 | 0 | 10 | — | 85 | — |
| 21.2 | 0 | 25 | — | 95 | — |
| 0 | 35 | 0 | — | 0 | — |
| 5.3 | 35 | 20 | 10 | 85 | 65 |
| 10.6 | 35 | 25 | 10 | 90 | 85 |
| 21.2 | 35 | 45 | 25 | 95 | 95 |

TABLE 17

Synergistic Activity of Foliar-Applied Compound A Benzyl Ester and Lamba Cyhalothrin Compositions on Weed Control in a Rice Cropping System.

| Compound A Benzyl Ester | Lambda cyhalothrin | Visual Weed Control (%) - 21 DAA | | | |
|---|---|---|---|---|---|
| | | IPOHE | | ECHCG | |
| g ae/ha | g ai/ha | Obs | Exp | Obs | Exp |
| 4.38 | 0 | 10 | — | 70 | — |
| 8.75 | 0 | 10 | — | 85 | — |
| 17.5 | 0 | 20 | — | 90 | — |
| 0 | 35 | 0 | — | 0 | — |
| 4.38 | 35 | 15 | 10 | 85 | 70 |
| 8.75 | 35 | 15 | 10 | 90 | 85 |
| 17.5 | 35 | 45 | 20 | 95 | 90 |

TABLE 18

Synergistic Activity of Foliar-Applied Compound A Benzyl Ester and Malathion Compositions on Weed Control in a Rice Cropping System.

| Compound A Benzyl Ester | Malathion | Visual Weed Control (%) - 22 DAA | | | | | | | |
|---|---|---|---|---|---|---|---|---|---|
| | | DIGSA | | ECHCG | | LEFCH | | LEFFA | LEFPA |
| g ae/ha | g ai/ha | Obs | Exp | Obs | Exp | Obs | Exp | | |
| 8 | 0 | 10 | — | 45 | — | 10 | — | | |
| 16 | 0 | 25 | — | 60 | — | 25 | — | | |
| 32 | 0 | 40 | — | 90 | — | 55 | — | | |
| 0 | 140 | 0 | — | 0 | — | 0 | — | | |
| 0 | 280 | 0 | — | 0 | — | 0 | — | | |
| 0 | 560 | 0 | — | 0 | — | 0 | — | | |
| 8 | 140 | 60 | 10 | 65 | 45 | 45 | 10 | | |
| 16 | 140 | 60 | 25 | 90 | 60 | 70 | 25 | | |
| 32 | 140 | 70 | 40 | 95 | 90 | 25 | 55 | | |
| 8 | 280 | 65 | 10 | 60 | 45 | 70 | 10 | | |
| 16 | 280 | 65 | 25 | 90 | 60 | 70 | 25 | | |
| 32 | 280 | 70 | 40 | 95 | 90 | 75 | 55 | | |
| 8 | 560 | 60 | 10 | 50 | 45 | 65 | 10 | | |
| 16 | 560 | 80 | 25 | 85 | 60 | 75 | 25 | | |
| 32 | 560 | 70 | 40 | 95 | 90 | 85 | 55 | | |

TABLE 18-continued

Synergistic Activity of Foliar-Applied Compound A Benzyl Ester and Malathion Compositions on Weed Control in a Rice Cropping System.

| Compound A Benzyl Ester | Malathion | Visual Weed Control (%) - 22 DAA | | | | | | | |
|---|---|---|---|---|---|---|---|---|---|
| | | DIGSA | | LEFCH | | LEFFA | | LEFPA | |
| g ae/ha | g ai/ha | Obs | Exp | Obs | Exp | Obs | Exp | Obs | Exp |
| 8 | 0 | 13 | — | 18 | — | 23 | — | 5 | — |
| 16 | 0 | 18 | — | 43 | — | 30 | — | 0 | — |
| 32 | 0 | 28 | — | 53 | — | 45 | — | 38 | — |
| 0 | 140 | 0 | — | 0 | — | 0 | — | 0 | — |
| 0 | 280 | 0 | — | 0 | — | 0 | — | 0 | — |
| 0 | 560 | 0 | — | 0 | — | 0 | — | 0 | — |
| 8 | 140 | 50 | 13 | 43 | 18 | 48 | 23 | 23 | 5 |
| 16 | 140 | 53 | 18 | 63 | 43 | 65 | 30 | 23 | 0 |
| 32 | 140 | 53 | 28 | 65 | 53 | 73 | 45 | 33 | 38 |
| 8 | 280 | 60 | 13 | 55 | 18 | 53 | 23 | 18 | 5 |
| 16 | 280 | 63 | 18 | 70 | 43 | 60 | 30 | 30 | 0 |
| 32 | 280 | 65 | 28 | 78 | 53 | 87 | 45 | 48 | 38 |
| 8 | 560 | 60 | 13 | 65 | 18 | 75 | 23 | 28 | 5 |
| 16 | 560 | 65 | 18 | 70 | 43 | 75 | 30 | 28 | 0 |
| 32 | 560 | 68 | 28 | 80 | 53 | 78 | 45 | 53 | 38 |

TABLE 19

Synergistic Activity of Foliar-Applied Compound A Benzyl Ester and Methamidophos Compositions on Weed Control in a Rice Cropping System.

| Compound A Benzyl Ester | Methamidophos | Visual Weed Control (%) - 19 DAA | | | |
|---|---|---|---|---|---|
| | | ECHCO | | IPOHE | |
| g ae/ha | g ai/ha | Obs | Exp | Obs | Exp |
| 8 | 0 | 65 | — | 20 | — |
| 16 | 0 | 90 | — | 40 | — |
| 32 | 0 | 95 | — | 50 | — |
| 0 | 112 | 0 | — | 0 | — |
| 0 | 224 | 0 | — | 0 | — |
| 8 | 112 | 85 | 65 | 25 | 20 |
| 16 | 112 | 95 | 90 | 45 | 40 |
| 32 | 112 | 95 | 95 | 65 | 50 |
| 8 | 224 | 85 | 65 | 10 | 20 |
| 16 | 224 | 90 | 90 | 55 | 40 |
| 32 | 224 | 95 | 95 | 60 | 50 |

TABLE 20

Synergistic Activity of Foliar-Applied Compound A Benzyl Ester and Piperonyl Butoxide Compositions on Weed Control in a Rice Cropping System.

| Compound A Benzyl Ester | Piperonyl Butoxide | Visual Weed Control (%) - 22 DAA | | | | | | | |
|---|---|---|---|---|---|---|---|---|---|
| | | DIGSA | | LEFCH | | LEFFA | | LEFPA | |
| g ae/ha | g ai/ha | Obs | Exp | Obs | Exp | Obs | Exp | Obs | Exp |
| 8 | 0 | 13 | — | 18 | — | 23 | — | 5 | — |
| 16 | 0 | 18 | — | 43 | — | 30 | — | 0 | — |
| 32 | 0 | 28 | — | 53 | — | 45 | — | 38 | — |
| 0 | 140 | 0 | — | 0 | — | 0 | — | 0 | — |
| 0 | 280 | 0 | — | 0 | — | 5 | — | 5 | — |
| 0 | 560 | 0 | — | 0 | — | 0 | — | 0 | — |
| 8 | 140 | 40 | 13 | 43 | 18 | 55 | 23 | 15 | 5 |

TABLE 20-continued

Synergistic Activity of Foliar-Applied Compound A Benzyl Ester and Piperonyl Butoxide Compositions on Weed Control in a Rice Cropping System.

| | | | | | | | | | |
|---|---|---|---|---|---|---|---|---|---|
| 16 | 140 | 43 | 18 | 58 | 43 | 65 | 30 | 23 | 0 |
| 32 | 140 | 48 | 28 | 70 | 53 | 75 | 45 | 35 | 38 |
| 8  | 280 | 45 | 13 | 45 | 18 | 48 | 26 | 28 | 10 |
| 16 | 280 | 53 | 18 | 55 | 43 | 65 | 34 | 30 | 5 |
| 32 | 280 | 55 | 28 | 75 | 53 | 75 | 48 | 75 | 41 |
| 8  | 560 | 43 | 13 | 55 | 18 | 58 | 23 | 40 | 5 |
| 16 | 560 | 53 | 18 | 63 | 43 | 70 | 30 | 48 | 0 |
| 32 | 560 | 55 | 28 | 65 | 53 | 75 | 45 | 53 | 38 |

TABLE 21

Synergistic Activity of Foliar-Applied Compound A Benzyl Ester and Spinetoram Compositions on Weed Control in a Rice Cropping System.

| Compound A Benzyl Ester | Spinetoram | Visual Weed Control (%) - 19 DAA | | | |
|---|---|---|---|---|---|
| | | ECHCO | | LEFCH | |
| g ae/ha | g ai/ha | Obs | Exp | Obs | Exp |
| 8  | 0   | 65 | —  | 45 | —  |
| 16 | 0   | 90 | —  | 45 | —  |
| 32 | 0   | 95 | —  | 50 | —  |
| 0  | 30  | 0  | —  | 0  | —  |
| 0  | 60  | 0  | —  | 0  | —  |
| 0  | 120 | 0  | —  | 0  | —  |
| 8  | 30  | 90 | 65 | 50 | 45 |
| 16 | 30  | 95 | 90 | 55 | 45 |
| 32 | 30  | 95 | 95 | 60 | 50 |
| 8  | 60  | 90 | 65 | 45 | 45 |
| 16 | 60  | 95 | 90 | 50 | 45 |
| 32 | 60  | 95 | 95 | 70 | 50 |
| 8  | 120 | 90 | 65 | 55 | 45 |
| 16 | 120 | 95 | 90 | 45 | 45 |
| 32 | 120 | 95 | 95 | 70 | 50 |

TABLE 22

Synergistic Activity of Foliar-Applied Compound A Benzyl Ester and Spinosad Compositions on Weed Control in a Rice Cropping System.

| Compound A Benzyl Ester | Spinosad | Visual Weed Control (%) - 21 DAA LEFCH | |
|---|---|---|---|
| g ae/ha | g ai/ha | Obs | Exp |
| 8  | 0   | 15 | — |
| 16 | 0   | 15 | — |
| 32 | 0   | 25 | — |
| 0  | 140 | 0  | — |
| 0  | 280 | 0  | — |
| 8  | 140 | 0  | 15 |
| 16 | 140 | 15 | 15 |
| 32 | 140 | 50 | 25 |
| 8  | 280 | 35 | 15 |
| 16 | 280 | 35 | 15 |
| 32 | 280 | 50 | 25 |

| Compound A Benzyl Ester | Spinosad | Visual Weed Control (%) - 21 DAA IPOHE | |
|---|---|---|---|
| g ae/ha | g ai/ha | Obs | Exp |
| 8 | 0   | 10 | — |
| 0 | 70  | 0  | — |
| 0 | 140 | 0  | — |
| 0 | 280 | 0  | — |
| 8 | 70  | 30 | 10 |

TABLE 22-continued

Synergistic Activity of Foliar-Applied Compound A Benzyl Ester and Spinosad Compositions on Weed Control in a Rice Cropping System.

| | | | |
|---|---|---|---|
| 8 | 140 | 20 | 10 |
| 8 | 280 | 25 | 10 |

TABLE 23

Synergistic Activity of Foliar-Applied Compound A Benzyl Ester and Sulfoxaflor Compositions on Weed Control in a Rice Cropping System.

| Compound A Acid | Sulfoxaflor | Visual Weed Control (%) - 21 DAA ECHCO | |
|---|---|---|---|
| g ae/ha | g ai/ha | Obs | Exp |
| 4.38 | 0    | 60 | — |
| 8.75 | 0    | 90 | — |
| 17.5 | 0    | 95 | — |
| 0    | 12.5 | 0  | — |
| 0    | 25   | 0  | — |
| 0    | 50   | 0  | — |
| 4.38 | 12.5 | 85 | 60 |
| 8.75 | 12.5 | 95 | 90 |
| 17.5 | 12.5 | 99 | 95 |
| 4.38 | 25   | 90 | 60 |
| 8.75 | 25   | 90 | 90 |
| 17.5 | 25   | 95 | 95 |
| 4.38 | 50   | 80 | 60 |
| 8.75 | 50   | 95 | 90 |
| 17.5 | 50   | 95 | 95 |

| Compound A Acid | Sulfoxaflor | Visual Weed Control (%) - 21 DAA LEFCH | |
|---|---|---|---|
| g ae/ha | g ai/ha | Obs | Exp |
| 8.75 | 0  | 30 | — |
| 17.5 | 0  | 30 | — |
| 0    | 25 | 0  | — |
| 0    | 50 | 0  | — |
| 8.75 | 25 | 20 | 30 |
| 17.5 | 25 | 70 | 30 |
| 8.75 | 50 | 50 | 30 |
| 17.5 | 50 | 60 | 30 |

| Compound A Benzyl Ester | Sulfoxaflor | Visual Weed Control (%) - 21 DAA LEFCH | |
|---|---|---|---|
| g ae/ha | g ai/ha | Obs | Exp |
| 17.5 | 0    | 50 | — |
| 0    | 12.5 | 0  | — |
| 0    | 25   | 0  | — |
| 0    | 50   | 0  | — |
| 17.5 | 12.5 | 55 | 50 |
| 17.5 | 25   | 90 | 50 |
| 17.5 | 50   | 85 | 50 |

| Compound A Benzyl Ester | Sulfoxaflor | Visual Weed Control (%) - 21 DAA LEFCH | |
|---|---|---|---|
| g ae/ha | g ai/ha | Obs | Exp |
| 16 | 0    | 15 | — |
| 0  | 37.5 | 0  | — |
| 0  | 75   | 0  | — |
| 0  | 150  | 0  | — |
| 16 | 37.5 | 25 | 15 |
| 16 | 75   | 15 | 15 |
| 16 | 150  | 50 | 15 |

TABLE 23-continued

Synergistic Activity of Foliar-Applied Compound A Benzyl Ester and Sulfoxaflor Compositions on Weed Control in a Rice Cropping System.

| Compound A Benzyl Ester | Sulfoxaflor | Visual Weed Control (%) - 21 DAA CYPIR | |
|---|---|---|---|
| g ae/ha | g ai/ha | Obs | Exp |
| 8 | 0 | 50 | — |
| 0 | 75 | 0 | — |
| 0 | 150 | 0 | — |
| 8 | 75 | 100 | 50 |
| 8 | 150 | 100 | 50 |

TABLE 24

Synergistic Activity of Foliar-Applied Compound A Benzyl Ester and Triazophos Compositions on Weed Control in a Rice Cropping System.

| Compound A Benzyl Ester | Triazophos | Visual Weed Control (%) - 22 DAA | | | | | |
|---|---|---|---|---|---|---|---|
| | | DIGSA | | ECHCG | | LEFCH | |
| g ae/ha | g ai/ha | Obs | Exp | Obs | Exp | Obs | Exp |
| 8 | 0 | 10 | — | 50 | — | 25 | — |
| 16 | 0 | 20 | — | 60 | — | 30 | — |
| 32 | 0 | 25 | — | 95 | — | 60 | — |
| 0 | 100 | 0 | — | 0 | — | 0 | — |
| 0 | 200 | 0 | — | 0 | — | 0 | — |
| 8 | 100 | 50 | 10 | 65 | 50 | 50 | 25 |
| 16 | 100 | 60 | 20 | 85 | 60 | 60 | 30 |
| 32 | 100 | 65 | 25 | 95 | 95 | 75 | 60 |
| 8 | 200 | 55 | 10 | 60 | 50 | 60 | 25 |
| 16 | 200 | 60 | 20 | 65 | 60 | 65 | 30 |
| 32 | 200 | 65 | 25 | 95 | 95 | 75 | 60 |

| Compound A Benzyl Ester | Triazophos | Visual Weed Control (%) - 22 DAA IPOHE | |
|---|---|---|---|
| g ae/ha | g ai/ha | Obs | Exp |
| 16 | 0 | 10 | — |
| 32 | 0 | 35 | — |
| 0 | 100 | 0 | — |
| 0 | 200 | 0 | — |
| 16 | 100 | 30 | 10 |
| 32 | 100 | 30 | 35 |
| 16 | 200 | 30 | 10 |
| 32 | 200 | 50 | 35 |

| Compound A Benzyl Ester | Triazophos | Visual Weed Control (%) - 22 DAA CYPES | |
|---|---|---|---|
| g ae/ha | g ai/ha | Obs | Exp |
| 8 | 0 | 70 | — |
| 0 | 100 | 0 | — |
| 0 | 200 | 0 | — |
| 8 | 100 | 85 | 70 |
| 8 | 200 | 90 | 70 |

| Compound A Benzyl Ester | Triazophos | Visual Weed Control (%) - 19 DAA | | | | | |
|---|---|---|---|---|---|---|---|
| | | DIGSA | | ECHCO | | LEFCH | |
| g ae/ha | g ai/ha | Obs | Exp | Obs | Exp | Obs | Exp |
| 8 | 0 | 30 | — | 65 | — | 45 | — |
| 16 | 0 | 35 | — | 90 | — | 45 | — |
| 32 | 0 | 40 | — | 95 | — | 50 | — |
| 0 | 375 | 0 | — | 0 | — | 0 | — |
| 8 | 375 | 60 | 30 | 85 | 65 | 55 | 45 |
| 16 | 375 | 40 | 35 | 95 | 90 | 80 | 45 |
| 32 | 375 | 70 | 40 | 95 | 95 | 80 | 50 |

BRAPP *Urochloa platyphylla* (Nash) R.D. Webster or *Brachiaria platyphylla* (Groseb.) Nash, broadleaf signalgrass.
CYPES *Cyperus esculentus* L., nutsedge, yellow
CYPIR *Cyperus iria* L., flatsedge, rice
DIGSA *Digitaria sanguinalis* (L.) Scop., crabgrass, large
ECHCG *Echinochloa crus-galli* (L.) Beauv., barnyardgrass
ECHCO *Echinochloa colona* (L.) Link, junglerice
IPOHE *Ipomoea hederacea* Jacq., morningglory, ivyleaf
LEFCH *Leptochloa chinensis* (L.) Nees, sprangletop, Chinese
LEFFA *Leptochloa fascicularis* (Lam.) Gray, sprangletop, bearded
LEFPA *Leptochloa panicoides* (Presl.) Hitchc., sprangletop, Amazon
SCPJU *Schoenoplectus juncoides* Roxb., bulrush, Japanese
g ae/ha = grams acid equivalent per hectare
g ai/ha = grams active ingredient per hectare
Obs = observed value
Exp = expected value as calculated by Colby's equation
DAA = days after application Example II Evaluation of in-Water Applied Herbicidal Mixtures for Weed Control in Transplanted Paddy Rice Weed seeds or nutlets of the desired test plant species were planted in puddled soil (mud) prepared by mixing a shredded, non-sterilized mineral soil (50.5 percent silt, 25.5 percent clay, and 24 percent sand, with a pH of about 7.6 and an organic matter content of about 2.9 percent) and water at a 1:1 volumetric ratio. The prepared mud was dispensed in 365 mL aliquots into 16-ounce (oz.) non-perforated plastic pots with a surface area of 86.59 square centimeters ($cm^2$) leaving a headspace of 3 centimeters (cm) in each pot. Rice seeds were planted in Sun Gro MetroMix® 306 planting mixture, which typically has a pH of 6.0 to 6.8 and an organic matter content of about 30 percent, in plastic plug trays. Seedlings at the second or third leaf stage of growth were transplanted into 860 mL of mud contained in 32-oz. non-perforated plastic pots with a surface area of 86.59 $cm^2$ 4 days prior to herbicide application. The paddy was created by filling the headspace of the pots with 2.5 to 3 cm of water. When required to ensure good germination and healthy plants, a fungicide treatment and/or other chemical or physical treatment was applied. The plants were grown for 4-22 days in a greenhouse with an approximate 14 h photoperiod which was maintained at about 29° C. during the day and about 26° C. during the night. Nutrients were added as Osmocote® (17:6:10, N:P:K+minor nutrients) at 2 grams (g) per 16-oz. pot and 4 g per 32-oz. pot. Water was added on a regular basis to maintain the paddy flood, and supplemental lighting was provided with overhead metal halide 1000-Watt lamps as necessary. The plants were employed for testing when they reached the first through fourth true leaf stage.

Treatments consisted of the acid or esters of 4-amino-3-chloro-5-fluoro-6-(4-chloro-2-fluoro-3-methoxy-phenyl)pyridine-2-carboxylic acid (compound A) each formulated as an SC (suspension concentrate) and various herbicidal components alone and in combination. Forms of compound A were applied on an acid equivalent basis.

Forms of compound A (compound of formula I) tested include:

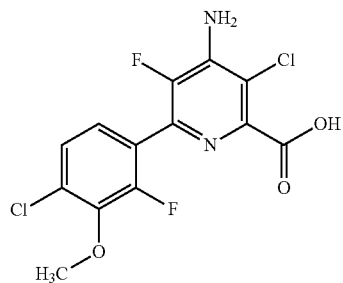

Compound A Acid

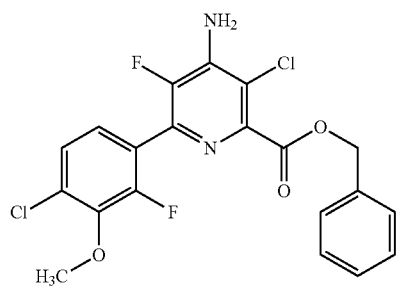

Compound A Benzyl Ester

Other herbicidal components were applied on an active ingredient basis and consisted of etofenprox (technical grade material) and sulfoxaflor formulated as Sulfoxaflor WG.

Treatment requirements for each compound or herbicidal component were calculated based upon the rates being tested, the concentration of active ingredient or acid equivalent in the formulation, an application volume of 2 mL per component per pot, and an application area of 86.59 cm² per pot.

For formulated compounds, a measured amount was placed in an individual 100 or 200 mL glass vial and was dissolved in a volume of 1.25% (v/v) AgriDex® crop oil concentrate to obtain application solutions. If the test compound did not dissolve readily, the mixture was warmed and/or sonicated.

For technical grade compounds, a weighed amount was placed in an individual 100 to 200 mL glass vial and was dissolved in a volume of acetone to obtain concentrated stock solutions. If the test compound did not dissolve readily, the mixture was warmed and/or sonicated. The concentrated stock solutions obtained were diluted with an equivalent volume of an aqueous mixture containing 2.5% (v/v) crop oil concentrate so that the final application solutions contained 1.25% (v/v) crop oil concentrate.

Applications were made by injecting with a pipetter appropriate amounts of the application solutions, individually and sequentially, into the aqueous layer of the paddy. Control plants were treated in the same manner with the solvent blank. Applications were made so that all treated plant material received the same concentrations of acetone and crop oil concentrate.

The treated plants and control plants were placed in a greenhouse as described above and water was added as needed to maintain a paddy flood. After approximately 3 weeks the condition of the test plants as compared with that of the untreated plants was determined visually and scored on a scale of 0 to 100 percent where 0 corresponds to no injury or growth inhibition and 100 corresponds to complete kill.

Colby's equation was used to determine the herbicidal effects expected from the mixtures (Colby, S. R. Calculation of the synergistic and antagonistic response of herbicide combinations. *Weeds* 1967, 15, 20-22.).

The following equation was used to calculate the expected activity of mixtures containing two active ingredients, A and B:

$$\text{Expected} = A + B - (A \times B / 100)$$

A=observed efficacy of active ingredient A at the same concentration as used in the mixture;
B=observed efficacy of active ingredient B at the same concentration as used in the mixture.

Some of the compounds tested, application rates employed, plant species tested, and results are given in Tables 25-27.

TABLE 25

Synergistic Activity of In-Water Applications of Compound A Benzyl Ester and Etofenprox Compositions on Weed Control in a Rice Cropping System.

| Compound A Benzyl Ester | Etofenprox | Visual Weed Control (%) - 21 DAA | | | |
|---|---|---|---|---|---|
| | | ECHCG | | CYPRO | |
| g ae/ha | g ai/ha | Obs | Exp | Obs | Exp |
| 8 | 0 | 40 | — | 40 | — |
| 0 | 75 | 0 | — | 0 | — |
| 0 | 150 | 0 | — | 0 | — |
| 0 | 300 | 0 | — | 0 | — |
| 8 | 75 | 40 | 40 | 75 | 40 |
| 8 | 150 | 75 | 40 | 30 | 40 |
| 8 | 300 | 90 | 40 | 70 | 40 |

TABLE 26

Synergistic Activity of In-Water Applications of Compound A Acid and Sulfoxaflor Compositions on Weed Control in a Rice Cropping System.

| Compound A Acid | Sulfoxaflor | Visual Weed Control (%) - 21 DAA SCPMA | |
|---|---|---|---|
| g ae/ha | g ai/ha | Obs | Exp |
| 4.38 | 0 | 0 | — |
| 8.75 | 0 | 0 | — |
| 0 | 50 | 0 | — |
| 4.38 | 50 | 100 | 0 |
| 8.75 | 50 | 100 | 0 |

TABLE 27

Synergistic Activity of In-Water Applications of Compound A Benzyl Ester and Sulfoxaflor Compositions on Weed Control in a Rice Cropping System.

| Compound A Benzyl Ester | Sulfoxaflor | Visual Weed Control (%) - 21 DAA SCPMA | |
|---|---|---|---|
| g ae/ha | g ai/ha | Obs | Exp |
| 4.38 | 0 | 0 | — |
| 8.75 | 0 | 0 | — |
| 17.5 | 0 | 0 | — |
| 0 | 50 | 0 | — |
| 4.38 | 50 | 0 | 0 |

TABLE 27-continued

Synergistic Activity of In-Water Applications of Compound A Benzyl Ester and Sulfoxaflor Compositions on Weed Control in a Rice Cropping System.

| 8.75 | 50 | 100 | 0 |
| 17.5 | 50 | 95 | 0 |

| Compound A Benzyl Ester | Sulfoxaflor | Visual Weed Control (%) - 19 DAA LEFCH | |
|---|---|---|---|
| g ae/ha | g ai/ha | Obs | Exp |
| 8 | 0 | 3 | — |
| 16 | 0 | 8 | — |
| 32 | 0 | 10 | — |
| 0 | 150 | 0 | — |
| 8 | 150 | 8 | 3 |
| 16 | 150 | 20 | 8 |
| 32 | 150 | 25 | 10 |

| Compound A Benzyl Ester | Sulfoxaflor | Visual Weed Control (%) - 19 DAA CYPRO | |
|---|---|---|---|
| g ae/ha | g ai/ha | Obs | Exp |
| 8 | 0 | 20 | — |
| 16 | 0 | 88 | — |
| 32 | 0 | 87 | — |
| 0 | 37.5 | 0 | — |
| 0 | 75 | 0 | — |
| 0 | 150 | 0 | — |
| 8 | 37.5 | 73 | 20 |
| 16 | 37.5 | 70 | 88 |
| 32 | 37.5 | 100 | 87 |
| 8 | 75 | 58 | 20 |
| 16 | 75 | 85 | 88 |
| 32 | 75 | 100 | 87 |
| 8 | 150 | 40 | 20 |
| 16 | 150 | 75 | 88 |
| 32 | 150 | 90 | 87 |

CYPRO *Cyperus rotundus* L., nutsedge, purple
ECHCG *Echinochloa crus-galli* (L.) Beauv., barnyardgrass
LEFCH *Leptochloa chinensis* (L.) Nees, sprangletop, Chinese
SCPMA *Bolboschoenus maritimus* (L.) Palla, clubrush, sea
g ae/ha = grams acid equivalent per hectare
g ai/ha = grams active ingredient per hectare
Obs = observed value
Exp = expected value as calculated by Colby's equation
DAA = days after application The present invention is not limited in scope by the embodiments disclosed herein which are intended as illustrations of a few aspects of the invention and any embodiments which are functionally equivalent are within the scope of this invention. Various modifications of the compositions and methods in addition to those shown and described herein will become apparent to those skilled in the art and are intended to fall within the scope of the appended claims. Further, while only certain representative combinations of the composition components and method steps disclosed herein are specifically discussed in the embodiments above, other combinations of the composition components and method steps will become apparent to those skilled in the art and also are intended to fall within the scope of the appended claims. Thus a combination of components or method steps may be explicitly mentioned herein; however, other combinations of components and method steps are included, even though not explicitly stated. The term comprising and variations thereof as used herein is used synonymously with the term including and variations thereof and are open, non-limiting terms.

What is claimed is:

1. A herbicidal composition comprising a synergistically herbicidally effective amount of (a) a compound of the formula (I)

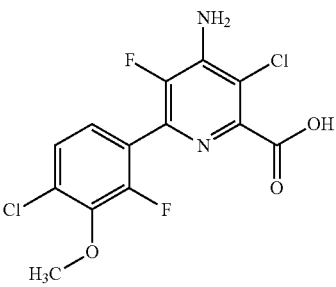

or an agriculturally acceptable salt or ester thereof and (b) an insecticide, wherein the insecticide is acephate, carbaryl, carbofuran, cartap, chlorpyrifos, cypermethrin, dimethoate, dinotefuran, etofenprox, fenitrothion, fipronil, imidacloprid, lambda-cyhalothrin, malathion, methamidophos, piperonyl butoxide, spinetoram, spinosad, sulfoxaflor, or triazophos.

2. The composition of claim 1, wherein (a) is a $C_{1-4}$ alkyl or benzyl ester of compound (I).

3. The composition of claim 2, wherein (a) is a $C_{1-4}$ alkyl ester of compound (I).

4. The composition of claim 2, wherein (a) is a benzyl ester of compound (I).

5. The composition of claim 1, wherein (a) is the compound of formula (I), which is the carboxylic acid.

6. The composition of claim 1, further comprising a herbicide safener.

7. The composition of claim 1, wherein;
the weight ratio of compound of formula (I) or agriculturally acceptable salt or ester thereof to acephate is from about 1:1000 to about 6:1;
the weight ratio of compound of formula (I) or agriculturally acceptable salt or ester thereof to carbaryl is from about 1:500 to about 150:1;
the weight ratio of compound of formula (I) or agriculturally acceptable salt or ester thereof to carbofuran is from about 1:1500 to about 30:1;
the weight ratio of compound of formula (I) or agriculturally acceptable salt or ester thereof to cartap is from about 1:500 to about 1:1.5;
the weight ratio of compound of formula (I) or agriculturally acceptable salt or ester thereof to chlorpyrifos is from about 1:500 to about 15:1;
the weight ratio of compound of formula (I) or agriculturally acceptable salt or ester thereof to cypermethrin is from about 1:250 to about 150:1;
the weight ratio of compound of formula (I) or agriculturally acceptable salt or ester thereof to dimethoate is from about 1:500 to about 30:1;
the weight ratio of compound of formula (I) or agriculturally acceptable salt or ester thereof to dinotefuran is from about 1:500 to about 30:1;
the weight ratio of compound of formula (I) or agriculturally acceptable salt or ester thereof to etofenprox is from about 1:500 to about 30:1;
the weight ratio of compound of formula (I) or agriculturally acceptable salt or ester thereof to fenitrothion is from about 1:500 to about 30:1;

the weight ratio of compound of formula (I) or agriculturally acceptable salt or ester thereof to fipronil is from about 1:500 to about 300:1;

the weight ratio of compound of formula (I) or agriculturally acceptable salt or ester thereof to imidacloprid is from about 1:500 to about 60:1;

the weight ratio of compound of formula (I) or agriculturally acceptable salt or ester thereof to lambda-cyhalothrin is from about 1:500 to about 60:1;

the weight ratio of compound of formula (I) or agriculturally acceptable salt or ester thereof to malathion is from about 1:500 to about 150:1;

the weight ratio of compound of formula (I) or agriculturally acceptable salt or ester thereof to methamidophos is from about 1:1000 to about 30:1;

the weight ratio of compound of formula (I) or agriculturally acceptable salt or ester thereof to piperonyl butoxide is from about 1:1500 to about 150:1;

the weight ratio of compound of formula (I) or agriculturally acceptable salt or ester thereof to spinetoram is from about 1:500 to about 150:1;

the weight ratio of compound of formula (I) or agriculturally acceptable salt or ester thereof to spinosad is from about 1:500 to about 150:1;

the weight ratio of compound of formula (I) or agriculturally acceptable salt or ester thereof to sulfoxaflor is from about 1:500 to about 150:1; or the weight ratio of compound of formula (I) or agriculturally acceptable salt or ester thereof to triazophos is from about 1:500 to about 30:1.

8. The composition of claim 1, further comprising an agriculturally acceptable adjuvant or carrier.

9. The composition of claim 1, wherein the insecticide includes cartap and the cartap is cartap hydrochloride.

10. A method of controlling undesirable vegetation which comprises contacting the vegetation or the area adjacent to the vegetation with or applying to the soil or water to prevent the emergence or growth of the vegetation a synergistically herbicidally effective amount of (a) a compound of the formula (I)

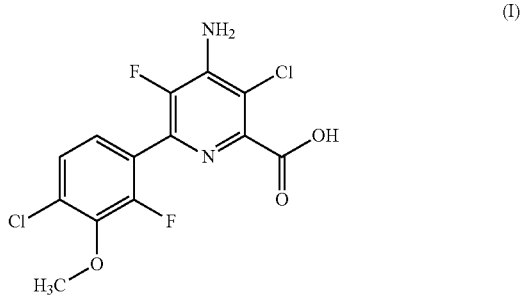 [SMILES: "(I)" ; COc1c(Cl)ccc(-c2nc(C(=O)O)c(Cl)c(N)c2F)c1F]

or an agriculturally acceptable salt or ester thereof and (b) an insecticide, wherein the insecticide is acephate, carbaryl, carbofuran, cartap, chlorpyrifos, cypermethrin, dimethoate, dinotefuran, etofenprox, fenitrothion, fipronil, imidacloprid, lambda-cyhalothrin, malathion, methamidophos, piperonyl butoxide, spinetoram, spinosad, sulfoxaflor, or triazophos.

11. The method of claim 10, wherein the undesirable vegetation is controlled in direct-seeded, water-seeded and transplanted rice, cereals, wheat, barley, oats, rye, *sorghum*, corn/maize, sugarcane, sunflower, oilseed rape, canola, sugar beet, soybean, cotton, pineapple, pastures, grasslands, rangelands, fallowland, turf, tree and vine orchards, plantation crops, vegetables, industrial vegetation management (IVM) and rights-of-way (ROW).

12. The method of claim 10, wherein the undesirable vegetation is immature.

13. The method of claim 10, wherein the (a) and (b) are applied to water.

14. The method of claim 13, wherein the water is part of a flooded rice paddy.

15. The method of claim 10, wherein the (a) and (b) are applied pre-emergently to the weed or crop.

16. The method of claim 10, wherein the (a) and (b) are applied post-emergently to the weed or crop.

17. The method of claim 10, wherein the undesirable vegetation is controlled in glyphosate-, 5-enolpyruvylshikimate-3-phosphate (EPSP) synthase inhibitor-, glufosinate-, glutamine synthetase inhibitor-, dicamba-, phenoxy auxin-, pyridyloxy auxin-, synthetic auxin-, auxin transport inhibitor-, aryloxyphenoxypropionate-, cyclohexanedione-, phenylpyrazoline-, acetyl CoA carboxylase (ACCase) inhibitor-, imidazolinone-, sulfonylurea-, pyrimidinylthiobenzoate-, triazolopyrimidine-, sulfonylaminocarbonyltriazolinone-, acetolactate synthase (ALS) or acetohydroxy acid synthase (AHAS) inhibitor-, 4-hydroxyphenyl-pyruvate dioxygenase (HPPD) inhibitor-, phytoene desaturase inhibitor-, carotenoid biosynthesis inhibitor-, protoporphyrinogen oxidase (PPO) inhibitor-, cellulose biosynthesis inhibitor-, mitosis inhibitor-, microtubule inhibitor-, very long chain fatty acid inhibitor-, fatty acid and lipid biosynthesis inhibitor-, photosystem I inhibitor-, photosystem II inhibitor-, triazine-, or bromoxynil-tolerant crops.

18. The method of claim 17, wherein the tolerant crop possesses multiple or stacked traits conferring tolerance to multiple herbicides or multiple modes of action.

19. The method of claim 10, wherein the undesirable vegetation comprises a herbicide resistant or tolerant weed.

20. The method of claim 19, wherein the resistant or tolerant weed is a biotype with resistance or tolerance to multiple herbicides, or multiple herbicide modes-of-action or via multiple resistance mechanisms.

21. The method of claim 20, wherein the resistant or tolerant weed is a biotype resistant or tolerant to acetolactate synthase (ALS) or acetohydroxy acid synthase (AHAS) inhibitors, photosystem II inhibitors, acetyl CoA carboxylase (ACCase) inhibitors, synthetic auxins, auxin transport inhibitors, photosystem I inhibitors, 5-enolpyruvylshikimate-3-phosphate (EPSP) synthase inhibitors, microtubule assembly inhibitors, fatty acid and lipid synthesis inhibitors, protoporphyrinogen oxidase (PPO) inhibitors, carotenoid biosynthesis inhibitors, very long chain fatty acid (VLCFA) inhibitors, phytoene desaturase (PDS) inhibitors, glutamine synthetase inhibitors, 4-hydroxyphenyl-pyruvate-dioxygenase (HPPD) inhibitors, mitosis inhibitors, cellulose biosynthesis inhibitors, herbicides with multiple modes-of-action, quinclorac, arylaminopropionic acids, difenzoquat, endothall, or organoarsenicals.

* * * * *